US011478314B1

United States Patent
Roh et al.

(10) Patent No.: US 11,478,314 B1
(45) Date of Patent: Oct. 25, 2022

(54) SYSTEM AND METHOD FOR IMPLANTING SMART IMPLANTS USING ROBOTIC TELESURGERY

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael J. Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/835,869

(22) Filed: Jun. 8, 2022

(51) Int. Cl.
*A61B 34/35* (2016.01)
*A61B 90/00* (2016.01)
*A61B 34/10* (2016.01)
*A61B 34/20* (2016.01)
*A61B 34/00* (2016.01)
*A61B 34/30* (2016.01)

(52) U.S. Cl.
CPC .............. *A61B 34/35* (2016.02); *A61B 90/37* (2016.02); *A61B 2034/102* (2016.02); *A61B 2034/105* (2016.02); *A61B 2034/2048* (2016.02); *A61B 2034/2065* (2016.02); *A61B 2034/252* (2016.02); *A61B 2034/256* (2016.02); *A61B 2034/305* (2016.02)

(58) Field of Classification Search
CPC ...... A61B 2034/102; A61B 2034/2048; A61B 2034/2065; A61B 2034/256; A61B 2034/305; A61B 34/35; A61B 90/37; A61B 2034/105; A61B 2034/252
See application file for complete search history.

(56) References Cited

U.S. PATENT DOCUMENTS

| 10,902,944 B1 * | 1/2021 | Casey | G16H 20/40 |
| 2020/0281742 A1 * | 9/2020 | Wu | A61F 2/46 |
| 2021/0137613 A1 * | 5/2021 | Chi | A61B 34/30 |

* cited by examiner

*Primary Examiner* — Kevin T Truong
*Assistant Examiner* — Diana Jones
(74) *Attorney, Agent, or Firm* — Fish & Richardson P.C.

(57) ABSTRACT

A system for using robotic telesurgery to implant a smart implant is disclosed. The system comprises a remote doctor module communicatively coupled with an operating room module over a cloud network. The operating room module comprises a robotic arm, a processor, and communication interface which communicates with the smart implant during the surgical procedure. The Operating Room Module testing the smart implant prior to implantation surgery; correlating data collected during the implantation surgery against past data from previous surgeries; determining whether the plurality of sensors is working properly; and transferring communication with the smart implant to a user device receive and monitor data from the plurality of sensors integrated into the smart implant to determine the smart implant is operating according as expected and to monitor the patient's condition.

20 Claims, 18 Drawing Sheets

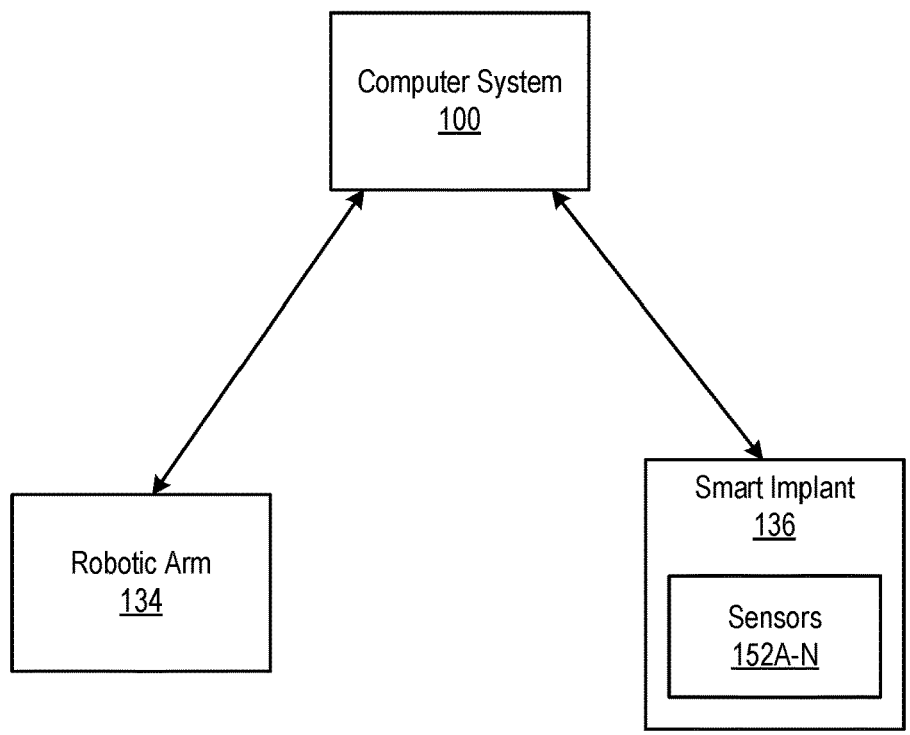
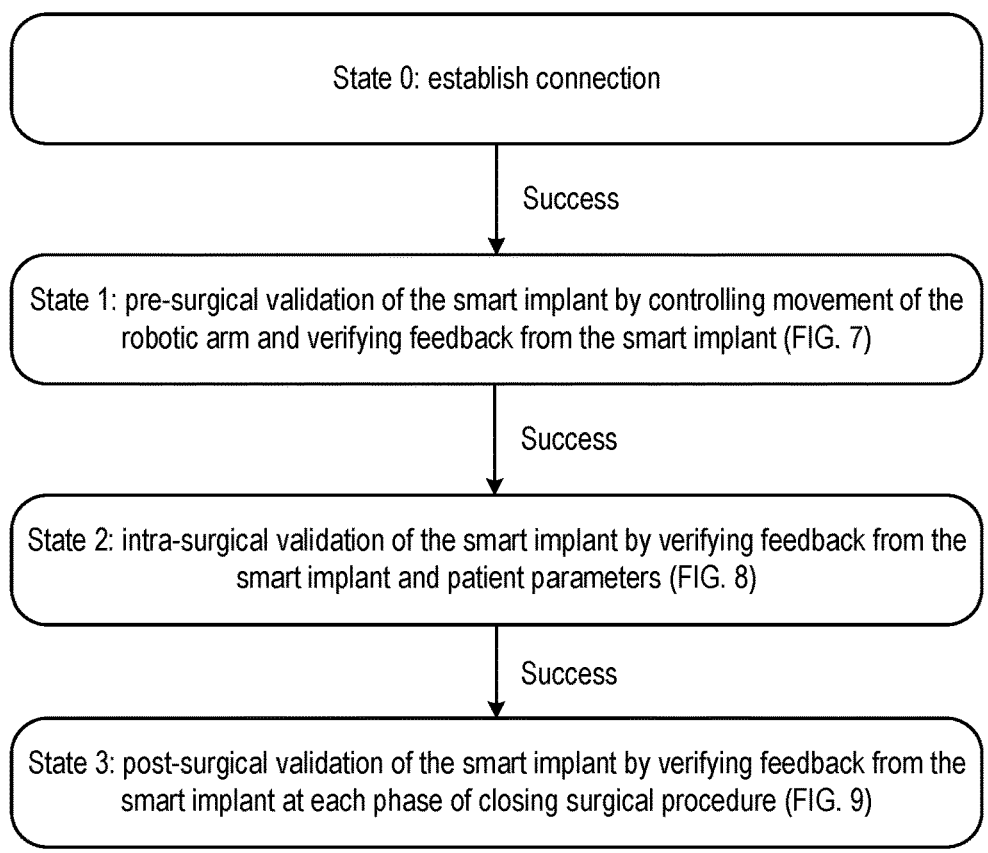
FIG. 1C

| REMOTE DATABASE (SMART KNEE IMPLANT IMPLANTED) | | | | | | | |
|---|---|---|---|---|---|---|---|
| PATIENT NAME | TIME | TEMPERA-TURE (THRESHOLD OF 36.5°C) | ORIENTATION OF THE ROBOTIC ARM | ORIENTATION OF THE SMART KNEE IMPLANT | HEART RATE-BLOOD PRESSURE (THRESHOLD 60-100) (bpm)-(120/80) | FORCE EXERTED BY SMART IMPLANT (100lbs-500lbs) | RANGE OF MOTION (ROM) THRESHOLD RANGE 30° to 180° between flexion extension and hyperextension |
| PATIENT 1 | 12:22:10 PM | 36.5 | 12cm, 09cm, 11cm | 12cm, 10cm, 11cm | 84-100/80 | 50 | 30° to 150° |
|  | 12:22:20 PM | 36.4 | 13cm, 10cm, 10cm | 10cm, 10cm, 10cm | 92-105/85 | 90 | 30° to 180° |
|  | 12:22:30 PM | 36.4 | 14cm, 13cm, 10cm | 14cm, 12cm, 10cm | 80-90/60 | 100 | 20° to 25° |
|  | 12:22:40 PM | 36.4 | 15cm, 14cm, 10cm | 15cm, 14cm, 10cm | 89-90/75 | 120 | 40° to 170° |
|  | 12:22:50 PM | 36.4 | 14cm, 10cm, 12cm | 14cm, 10cm, 12cm | 85-120/70 | 250 | 30° to 40° |
|  | 12:22:55 PM | 36.4 | 11cm, 16cm, 12cm | 12cm, 12cm, 11cm | 92-110/72 | 290 | 30° to 50° |
| PATIENT 2 | 16:17:20 PM | 36.5 | 13cm, 10cm, 12cm | 13cm, 10cm, 12cm | 95-130/90 | 100 | 20° to 30° |
|  | 16:17:25 PM | 35.5 | 15cm, 14cm, 10cm | 15cm, 14cm, 10cm | 80-100/90 | 250 | 30° to 155° |

FIG. 2

| PATIENT NAME | TIME | TEMPERATURE | BLOOD PRESSURE | HEART RATE | STATUS OF SMART KNEE IMPLANT |
|---|---|---|---|---|---|
| ALEX | 12:22:10 PM | 36.5 | 100/80 | 84 | OFFLINE |
| | 12:22:20 PM | 36.4 | 105/85 | 92 | ACTIVE-NORMAL |
| | 16:17:20 PM | 38.5 | 90/60 | 80 | ACTIVE-NORMAL |
| | 16:17:25 PM | 35.5 | 90/75 | 89 | ACTIVE-ERROR |
| | 16:17:30 PM | 36.4 | 120/70 | 85 | ACTIVE-NORMAL |
| | 16:17:35 PM | 38.5 | 110/72 | 92 | ACTIVE-ERROR |

SYSTEM AND METHOD FOR IMPLANTING SMART IMPLANTS USING ROBOTIC TELESURGERY

TECHNICAL FIELD

This disclosure is generally related to systems and methods for performing surgical procedures to implant medical devices, such as smart implants positioned within a patient through robot-assisted surgical procedures.

BACKGROUND

During surgical procedures, surgeons can manually insert medical devices (also referred to as "implants") into a patient's body to provide therapeutic and/or diagnostic benefits during and after the surgical procedure. Typically, a surgeon must precisely insert and adjust the implant within the patient's body to ensure the surgical procedure is performed correctly and the implant provides the intended or expected benefits to the patient. Various types of implants have been used, such as sensory and neurological medical implants (e.g., intraocular lens, intrastromal corneal ring segment, cochlear implant, tympanostomy tube, and neurostimulator), cardiovascular implants (e.g., artificial heart, artificial heart valve, implantable cardioverter-defibrillator, cardiac pacemaker, and coronary stent), orthopedic implants (e.g., pins, rods, screws, plates), electrical implants (e.g., implant to deliver electrical stimulus to tissue and/or nerves within a patient, such as the vagus nerve), and/or other types of implants. "Smart implants" are a category of implantable medical devices that generally refer to implantable devices capable of providing therapeutic benefits along with electronic components that can provide diagnostic capabilities, such as implants with sensors, microcontrollers, and communication interfaces capable of providing real-time biofeedback for a patient.

Surgical procedures have been performed with the assistance of robotic systems, which refer to systems that provide intelligent services and information by interacting with their environment, including human beings, via the use of various sensors, actuators, and human interfaces. These are employed for automating processes in a wide range of applications, ranging from industrial (manufacturing), domestic, medical, service, military, entertainment, space, etc. The adoption of robotic systems provides several benefits, including efficiency and speed improvements, lower costs, and higher accuracy. Performing medical procedures with the assistance of robotic technology are referred to as medical robotic systems. The medical robotic system market can be segmented by product type into Surgical Robotic Systems, Rehabilitative Robotic Systems, Non-invasive Radiosurgery Robots, Hospital & Pharmacy Robotic Systems. Robotic technologies have offered valuable enhancements to medical or surgical processes through improved precision, stability, and dexterity. Robots in medicine help by relieving medical personnel from routine tasks, and by making medical procedures safer and less costly for patients. They can also perform accurate surgery in tiny places and transport dangerous substances. Robotic surgeries are performed using tele-manipulators, which use the surgeon's actions on one side to control the "effector" on the other side. A medical robotic system ensures precision and may be used for remotely controlled, minimally-invasive procedures. The systems comprise computer-controlled electromechanical devices that work in response to controls manipulated by the surgeons. Robotic systems can be integrated into the embodiments in a variety of manners.

SUMMARY

This document generally relates to improved systems, methods, and techniques for implanting smart implants during surgical procedures, such as during robot-assisted surgical procedures that involve the placement of one or more smart implants within a patient during the procedure. More specifically, the disclosed techniques can be used to validate that the smart implant is operating correctly and as expected before, during, and after the surgical procedure, and can also use real-time information from the smart implant to improve and better perform the surgical procedure, including better and more accurate placement of the smart implant within a patient to maximize therapeutic benefits. For example, the disclosed techniques can be used to validate connectivity between a smart implant having one or more sensors and remote computing systems before, during, and after a surgical procedure, which can ensure that the smart implant is operating correctly throughout and after the surgical procedure.

In addition, the disclosed techniques permit for surgeons (or other medical professionals) to perform surgical procedures remotely (e.g., when the surgeons are not in a same physical location as their patients undergoing the surgeries), also known as telesurgery, using robotic surgical systems such as robotic surgical devices (e.g., robotic arms). A robot surgical system can include one or more robotic arms, which can be controlled remotely by a surgeon, a controller (e.g., master controller or console), and a sensor system. During a surgical procedure, one or more sensors integrated into a smart implant can detect implant location and impingement to determine movement of the implant within the patient's body. The sensor detections can be used to generate more precise and accurate control commands for operating the robot surgical system and implanting the smart implant during the surgical procedure.

Artificial Intelligence and/or Machine Learning (AI/ML) techniques may also be used to generate precise and accurate control commands. As an illustrative example, inserting a pedicle screw in a vertebrae versus inserting a scalpel to make an incision require different force profiles on the end effector (e.g., the drill or scalpel, etc.). A library and/or dataset of force versus time data can be built and generated for various operations. The data can vary depending on the type of end effector, the type of operation, and other operation-specific information. This library and/or dataset can then be used to train one or more machine learning models to improve the force over time of whatever end effector is used during runtime in an operation. As another illustrative example, a library of optical images can be generated for a variety of different operations. Images in the library that include localization of various structures (e.g. bone, body organs, devices inside the body, etc.) can be used to train one or more models to generate accurate and precise haptic feedback to the surgeon who is manipulating the end effector. The one or more models described herein can be any type of machine learning models, including but not limited to correlation models, ordinary least squares, convolutional neural networks (CNNs), supervised machine learning, etc.

The disclosed techniques can be used as part of pre-surgical validation phases, intra-surgical validation phases, and post-surgical validation phases. For example, during a pre-surgical validation phase, the disclosed techniques can be performed to determine whether sensors of the smart implant are accurately detecting motion data while the smart implant is moved by the robotic surgical device, such as a robotic arm. During the pre-surgical validation phase, the robotic arm can be controlled to make various movements to determine whether the sensors of the smart implant are accurately detecting that movement. During an intra-surgical validation phase, the disclosed techniques can be performed to determine whether the sensors of the smart implant are accurately detecting data while the smart implant is being inserted into a patient by the robotic surgical device. During this phase, the disclosed techniques can also be used to monitor patient parameters and determine whether the patient is experiencing any adverse conditions during the surgical procedure. During a post-surgical validation phase, the disclosed techniques can be performed during each phase of closing the surgical procedure, to determine whether the smart implant is operating correctly. For example, the smart implant may be operating correctly if the sensors of the smart implant detect conditions of the smart implant and/or the patient while inserted inside the patient and then transmit those conditions to a computing system. If the smart implant is operating correctly during the post-surgical validation phase, it can be determined that the surgical procedure can be closed and the patient can be removed from anesthesia to return to their life. If, at any phase during closing of the surgical procedure, the smart implant is not operating correctly, then closing may be halted and one or more corrective actions can be taken, such as not stitching up a surgical site, performing another or returning to the surgical procedure to remove the smart implant, etc.

As an illustrative example, sensor detections can be used for assessing hip arthroplasty component movement and/or a femoral head component movement, which may also fit in an acetabular component before, during, and after an implantation surgical procedure. The disclosed techniques, for example, can be used to determine information about a magnetic field from the sensor detections and output one or more indications of an orientation, coverage, and/or a force of the implant relative to other parts of the implant and/or parts of the patient's body, such as the femoral head component relative to the acetabular component. Using the disclosed techniques in surgical procedures, such as robotic telesurgery, the surgeon can more precisely implant a smart implant in the patient and ensure that the smart implant is operating effectively and as expected. After all, robotic telesurgery can reduce potential of human error that may arise when manually performing the surgical procedure because the sensor system can provide for real-time analysis of movement and orientation of the smart implant as it is being put into the patient's body. Real-time adjustments can be accurately made by the robot surgical system, under supervision of the surgeon, to ensure that the smart implant is properly placed inside the patient's body to provide therapeutic and/or diagnostic benefits.

The smart implants used with the disclosed techniques may also include embedded sensors that can provide real-time information to surgeons for accurate positioning of the implant during the surgical procedure as well as post-operative evaluation for better patient care throughout treatment and recovery. Smart implants may also reduce periprosthetic infection, which may arise with other types of implants used in orthopedic practice. As an illustrative example, a smart joint implant can include a prosthesis having a sensor array with multiple sensors. After a surgical procedure to implant the smart joint implant, the sensors can measure pressure of fluids in the patient's body that bathe the prosthesis. An electronics structure can receive this pressure data from the sensor array and wirelessly transmit the data to a remote receiver, computing system, or other device. The remote device that receives the data can then be configured to analyze the data and determine one or more treatment plans for the patient based on the pressure of fluids in the patient's body and around/over the prosthesis.

One or more embodiments described herein can include a method of implanting a smart implant during a surgical procedure using a robotic surgical device, the method including: establishing, by a computing system, a connection between a smart implant and the computing system, before performing a surgical procedure that includes implanting the smart implant in a patient using a robotic surgical device, testing the smart implant using the robotic surgical device, in which the testing includes: transmitting, by the computing system, instructions to the robotic surgical device that cause the robotic surgical device to perform a smart implant action, the smart implant action including at least moving the smart implant through one or more physical movements identified by the instructions, receiving, by the computing system via the connection, smart implant action data from at least one sensor of the smart implant while the smart implant action is performed by the robotic surgical device, and validating, by the computing system, pre-surgical operation of the smart implant based, at least in part, on the smart implant action data. The method can also include: during the surgical procedure, validating intra-surgical operation of the smart implant as the smart implant is inserted into the patient by the robotic surgical device, in which validating intra-surgical operation includes: receiving, by the computing system, intra-surgical data sensed by the at least one sensor of the smart implant as the smart implant is inserted into the patient, comparing, by the computing system, the received intra-surgical data with target data for the surgical procedure, and validating, by the computing system, intra-surgical operation of the smart implant and correct placement of the smart implant within the patient based, at least in part, on the comparison of the intra-surgical data with the target data. The method can also include, after the surgical procedure has been completed, validating post-surgical operation of the smart implant based, at least in part, on post-surgical data received from the smart implant.

In some implementations, the embodiments described herein can optionally include one or more of the following features. For example, the surgical procedure can include a robotic telesurgery procedure. The method can include continuously verifying, by the computing system, the connection between the smart implant and the computing system before, during, and after the surgical procedure, in which validating the pre-surgical operation of the smart implant is further based on the continuous verification of the connection before performing the surgical procedure, validating the intra-surgical operation of the smart implant is further based on the continuous verification of the connection during the surgical procedure, and validating the post-surgical operation of the smart implant is further based on the continuous verification of the connection after the surgical procedure. In some implementations, validating the pre-surgical operation of the smart implant can include correlating detected movement of the smart based on the smart implant movement data with the instructions for moving the robotic surgical device.

In some implementations, the robotic surgical device can include a robotic arm that is controlled by the computing system. During the pre-surgical testing and the intra-surgical operation validation, the computing system can be remote from at least one of the patient, the smart implant, and the robotic surgical device during the testing. The robotic surgical device before the surgical procedure can be the same robotic surgical device as during the surgical procedure. The testing of the smart implant can occur before the smart implant is inserted into the patient. The target data can include one or more expected data values corresponding to one or more of the patient, the surgical robot, and the surgical procedure. The at least one sensor can be at least one of a motion sensor, temperature sensor, and ECG monitoring sensor.

As another example, validating the intra-surgical operation of the smart implant further can include: receiving detected patient conditions during the surgical procedure from the at least one sensor of the smart implant, comparing the received patient conditions to expected patient conditions that are included in the target data, and determining, based on the comparison, whether the received patient conditions are within a threshold range of the expected patient conditions. The method can also include, in response to determining that the patient conditions are outside of the threshold range, generating, by the computing system, a notification indicating that the patient is trending outside of the threshold range and identifying corrective action to be taken. The corrective action can include removing the smart implant from the patient.

In some implementations, after the surgical procedure, validating the post-surgical operation of the smart implant can include: executing connection tests of the smart implant intermittently during one or more phases of closing the surgical procedure, and determining, at each phase of closing the surgical procedure, that the smart implant operates according to one or more expected threshold conditions based on the post-surgical data collected from the at least one sensor. The one or more phases of closing the surgical procedure can include closing a surgical site of the patient, checking patient parameters, and waking up the patient from anesthesia. The method can also include generating, by the computing system, a notification that the smart implant does not operate according to the expected threshold conditions based on a determination that, at one of the phases, data collected from the at least one sensor is not received by the computing system, the notification including a corrective action. The corrective action can include stopping one or more remaining phases of closing the surgical procedure. In some implementations, the method can further include generating, by the computing system and based on the determination, a notification indicating that a next phase of closing the surgical procedure can be performed. After the surgical procedure, the smart implant can be implanted inside the patient and may no longer be retained by the robotic surgical device.

One or more embodiments described herein can include a system for implanting a smart implant during a surgical procedure using a robotic surgical device, the system including: a robotic surgical device that can implant a smart implant into a patient during a surgical procedure, and a computer system in communication with the robotic surgical device and the smart implant, the computer system being able to: establish a connection between a smart implant and the computer system, and before performing a surgical procedure that includes implanting the smart implant in a patient using the robotic surgical device, test the smart implant using the robotic surgical device, in which the testing includes: transmitting instructions to the robotic surgical device that cause the robotic surgical device to perform a smart implant action, the smart implant action including at least moving the smart implant through one or more physical movements identified by the instructions, receiving, via the connection, smart implant action data from at least one sensor of the smart implant while the smart implant action is performed by the robotic surgical device, and validating pre-surgical operation of the smart implant based, at least in part, on the smart implant action data. The computer system can also, during the surgical procedure, validate intra-surgical operation of the smart implant as the smart implant is inserted into the patient by the robotic surgical device, in which validating intra-surgical operation can include: receiving intra-surgical data sensed by the at least one sensor of the smart implant as the smart implant is inserted into the patient, comparing the received intra-surgical data with target data for the surgical procedure, and validating intra-surgical operation of the smart implant and correct placement of the smart implant within the patient based, at least in part, on the comparison of the intra-surgical data with the target data. The computer system can also, after the surgical procedure has been completed, validate post-surgical operation of the smart implant based, at least in part, on post-surgical data received from the smart implant.

The system can optionally include one or more of the abovementioned features.

The devices, system, and techniques described herein may provide one or more of the following advantages. For example, robotic telesurgery combines robotics, communication technology (e.g., high-speed data connections), and management information systems to provide accurate, safe, reliable, and cost-effective surgical procedures. Robotic telesurgery also allows for expertise of specialized surgeons to be available to patients worldwide, without the need for patients to travel beyond their local hospital or for surgeons to travel beyond their local hospital(s). Therefore, robotic telesurgery can provide different healthcare surgical services around the world with the ability to perform surgeries for patients at remote locations and using wireless communication. During a robotic telesurgery, the surgeon at a master site can control the robot surgical system during the surgical procedure by inputting/generating various control commands to the robot surgical system at a physical location of the surgical procedure. The surgeon can provide the control commands through a human system interface, which can include haptic devices (e.g., keyboard, mouse, microphone, joystick, etc.), headphones, and/or video consoles for audio-video feedback. As a result, robotic telesurgery can help fulfill shortages of surgeons in certain regions of the world and help reduce or eliminate geographical barriers that prevent timely and high-quality surgical intervention. Further, robotic telesurgery can improve safety of patients since the robot surgical system can provide for real-time monitoring and accurate adjustments during the surgical procedure that may otherwise be challenging to accomplish in a manual procedure performed by the surgeon where human error is possible.

As another example, smart implants can provide reliable and cost-effective surgical procedures compared to conventional implant surgeries. The integration of smart implants into clinical practice can minimize complications, decrease recovery times, decrease lost workdays after surgery, and reduce readmissions and corrective procedures. Smart implants can also provide therapeutic benefits to patients. Example therapeutic benefits can include personalized medicine, optimized care for individual patients, and improved outcomes while also reducing surgical, treatment, and recovery costs to both patients and healthcare facilities.

The disclosed techniques can also provide diagnostic benefits. For example, as diagnostic tools, smart implants can provide information characterizing an environment inside the patient's body that may otherwise be challenging to characterize. This information can provide objective quantitative data to tailor treatment, trigger transitions in care, and detect adverse events earlier, during the surgical procedure and also after the surgical procedure. Smart implants can also provide continuous monitoring of critical internal body parameters, parameters which can be used to guide treatments in real-time to ensure improved patient outcomes and safety.

The disclosed techniques can also be used to further develop in vivo pathophysiology, healing, implant-tissue interfaces, and biomechanics. Moreover, the disclosed techniques can be used to develop and improve existing implants and surgical techniques.

The details of one or more implementations are set forth in the accompanying drawings and the description below. Other features and advantages will be apparent from the description and drawings, and from the claims.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 1C is a state flow diagram for performing a surgical procedure using the disclosed techniques.

FIG. 2 illustrates a remote database for a remote doctor module for a robot surgical system.

FIG. 3 illustrates an operation database for an operating room for the robot surgical system.

Like reference symbols in the various drawings indicate like elements.

DETAILED DESCRIPTION

Figure 1A:
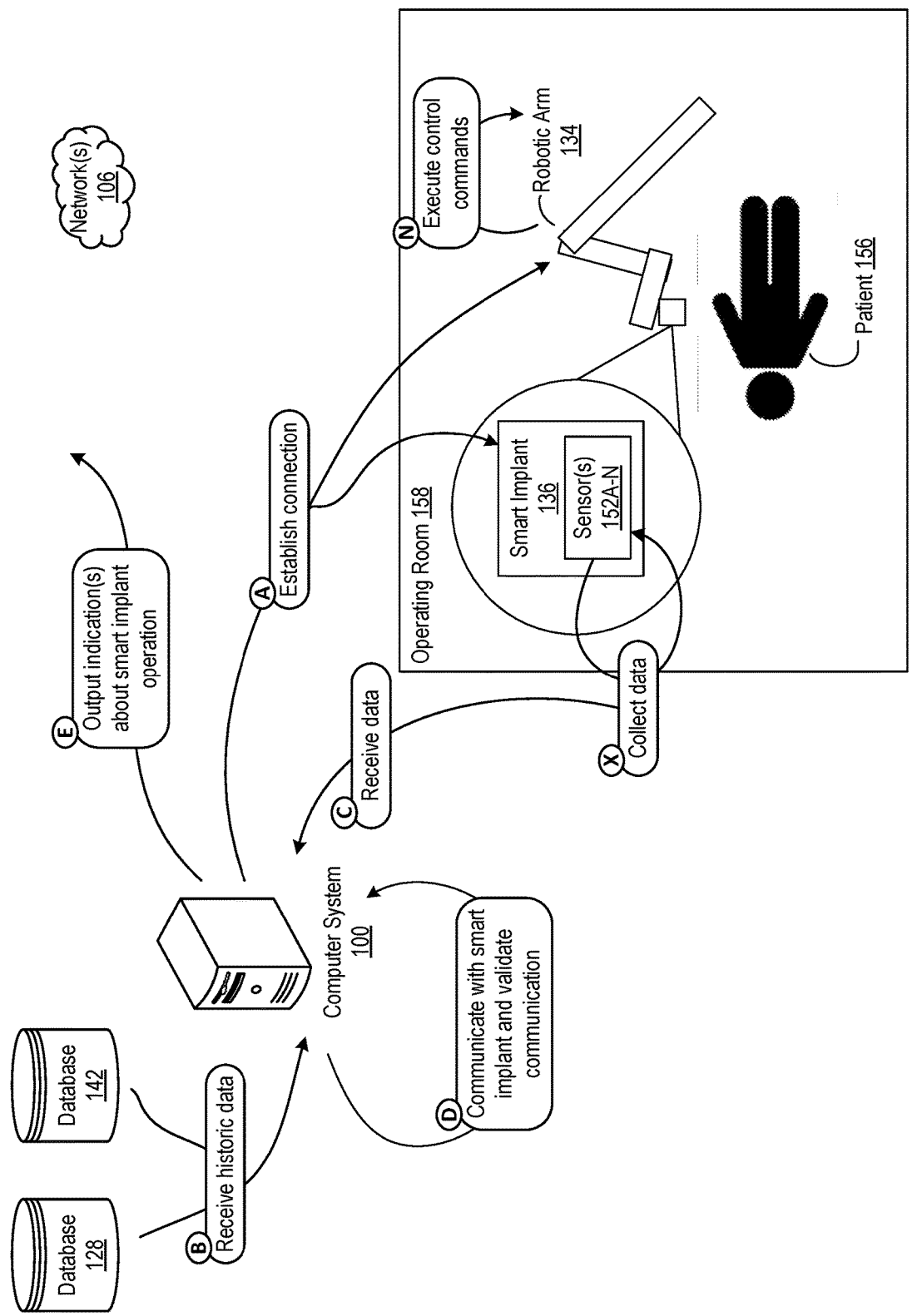
FIG. 1A is a conceptual diagram of a robot surgical system for performing a surgical procedure.

This document generally describes systems, methods, and techniques for performing a surgical procedure with a robot surgical system. More particularly, a surgeon or other medical professional can perform a surgical procedure for implanting a smart implant into a patient's body using the robot surgical system. Connection validation phases can be performed before, during, and after the surgical procedure to ensure that the smart implant is operatively correctly according to expected conditions for the smart implant and/or the patient. The surgical procedure can be a robotic telesurgery, as described herein. The surgical procedure can also be one or more other types of surgeries that can be performed with implants.

The surgeon can generate control commands at a computer system which can be transmitted to the robot surgical system. The robot surgical system can control components, such as robotic arms or other robotic surgical devices, to execute the commands, which can include accurately inserting the smart implant into the patient. The control commands can be generated based on computer analysis of data that is collected by sensors of the smart implant itself. The computer analysis can include use of AI/ML techniques for more accurate and precise control command generation and determination of whether the smart implant is operating according to expected conditions/parameters. For example, over time, data can be collected about force and speed or other time information at which end effectors and other surgical devices (e.g., robotic surgical devices, robotic arms, etc.) perform various types of operations. This data can be used to train one or more models to accurately and precisely generate control commands for such end effectors or other surgical devices during an operation. As another example, images captured during prior procedures can include localization of various structures (e.g. bone, body organs, devices inside the body, etc.), which can be used to train one or more models to generate accurate and precise haptic feedback to the surgeon who is manipulating the end effector or other surgical device. The one or more models described herein can be any type of machine learning models, including but not limited to correlation models, ordinary least squares, convolutional neural networks (CNNs), supervised machine learning, etc. Different models can be generated for different types of procedures/operations. Different models can also be generated for different types of end effectors or other surgical devices. In some implementations, different models can also be generated for different patient profiles, demographics, or other patient information (e.g., a robotic arm may be controlled differently on a child than a grown adult). Some embodiments of this disclosure, illustrating various of its features, may be discussed in further detail below. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It should also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure are described more fully hereinafter with reference to the accompanying figures in which like numerals represent like elements, and in which example embodiments are shown. Embodiments of the claims may be embodied in many different forms and should not be construed as limited to the embodiments set forth herein. The examples set forth herein are merely non-limiting examples among other possible examples. Moreover, although the disclosed techniques are described in reference to surgical procedures for inserting smart implants into patients, the disclosed techniques may also be applied to various other types of surgical procedures that may or may not include insertion of smart implants or other types of implants into patients.

Referring to the figures, FIG. 1A is a conceptual diagram of a robot surgical system for performing a surgical procedure. As described throughout this disclosure, the surgical procedure can be a robotic telesurgery. The surgical procedure can also be one or more other types of surgeries that may use robotic techniques and/or mechanisms to assist a surgeon in performing the surgeries.

Figure 1B:
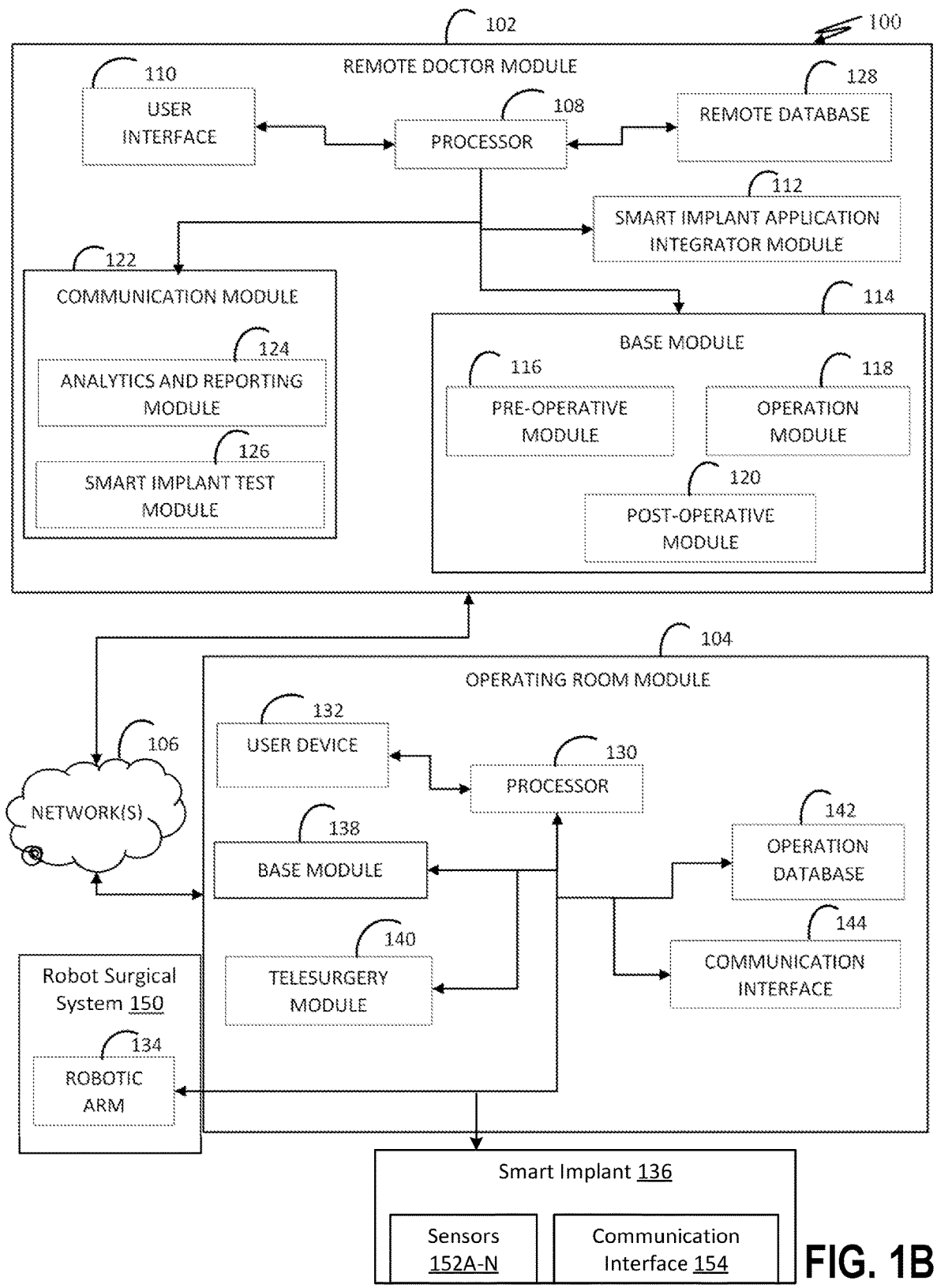
FIG. 1B illustrates a block diagram of a system for implanting a smart implant using robotic telesurgery.

Computer system 100 can communicate with a robotic arm 134, smart implant 136 having sensors 152A-N, and databases 128 and 142 via network(s) 106. Refer to FIG. 1B for additional discussion about the components described herein. The computer system 100 can include a remote doctor module and an operating room module. In some implementations, the computer system 100 may only include the remote doctor module or only the operating room module. As shown in FIG. 1A, the computer system 100 can be remote from an operating room 158. In some implementations, the computer system 100 may be in the operating room 158 or otherwise not remote form the operating room 158. In the operating room 158, the smart implant 136 can be surgically installed in patient 156 using tools such as the robotic arm 134. Staff, such as nurses or other practitioners can oversee installation of the smart implant 136, for example by the robotic arm 134. In some implementations, the staff can perform the installation using the robotic arm 134 as a guide or additional tool for precise and safe installation of the smart implant 136 in the patient 156.

Figure 4:
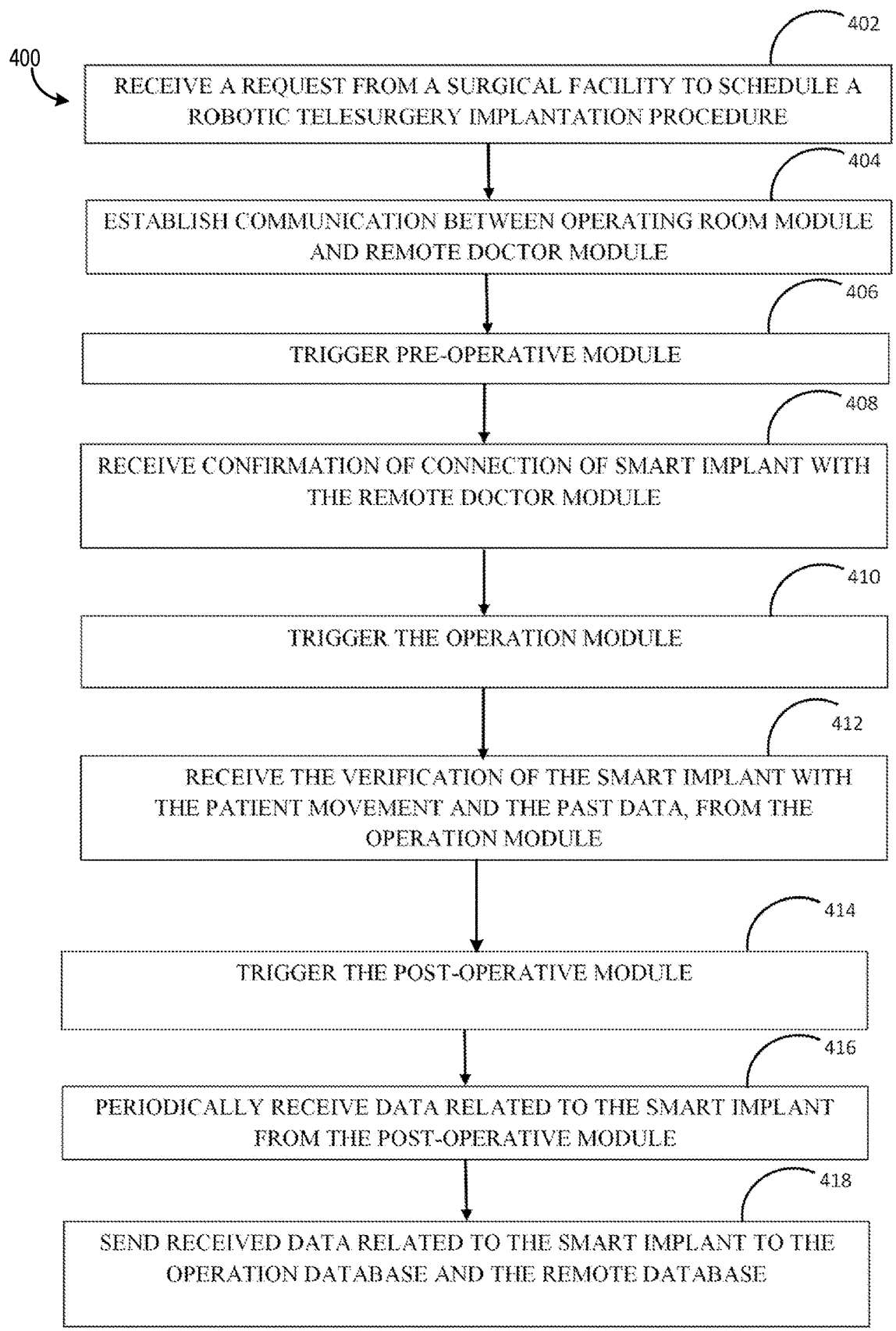
FIG. 4 is a flowchart of a process for operating a base module of the remote doctor module described herein.

During runtime (e.g., before, during, and/or after a surgical procedure), the computer system 100 can perform various validation phases to ensure communication and connection between components such as the smart implant 136 and the computer system 100. The computer system 100 can perform these validation phases to ensure that the sensors 152A-N of the smart implant 136 are functioning/ working properly, that the smart implant 136 is being appropriately installed in the patient 156, that the patient 156 continues to experience healthy/safe health conditions throughout the surgical procedure, and that the sensors 152A-N of the smart implant 136 function properly after the surgical procedure. Refer to FIG. 4 for additional discussion. The validation phases described herein can also be performed to check one or more other conditions of the smart implant 136 and/or the patient 156 before, during, and/or after the surgical procedure.

As shown in FIG. 1A, the computer system 100 can establish a connection with the smart implant 136 and the robotic arm 134 (block A). The computer system 100 may also receive historic data from the database 128 and/or the database 142 (block B). The historic data can indicate expected parameters for conditions that are sensed by the sensors 152A-N before, during, and/or after the surgical procedure. Block B can also be performed at any other time, for example, before block A, simultaneously with block A or one or more other blocks, and/or before or after any other blocks described in reference to FIG. 1A.

The computer system 100 may also continuously receive data from the sensors 152A-N of the smart implant 136 (block C) before, during, and after the surgical procedure. After all, the sensors 152A-N can be configured to collect data (block X) (e.g., continuously and/or at time intervals). Before, during, and after the surgical procedure, the robotic arm 134 may also execute control commands that may be generated by and received from the computer system 100 (block N). Block N can be performed before, during, or after any of the blocks described herein.

Moreover, the computer system 100 can generate the control commands using one or more machine learning-trained models, as described herein. The model(s) can be trained with data indicating force versus time of other robotic arms during other procedures. The other robotic arms can be a same type as the robotic arm 134. The other procedures can be same or similar as the procedure described in this FIG. 1A. Therefore, the model can use the data received from the sensors 152A-N and other procedure-related information and/or robotic arm information as input to determine accurate and precise control commands based on force versus time data. As another example, the model(s) can be trained with image data depicting localization of structures inside other patients. In some implementations, the other patients can have some similar demographics or other information as the patient 156. The model(s) can be trained to generate commands and/or haptic feedback assists the staff to avoid touching or interacting with similar structures inside the patient 156 when controlling/manipulating surgical devices used during the procedure.

Figure 7:
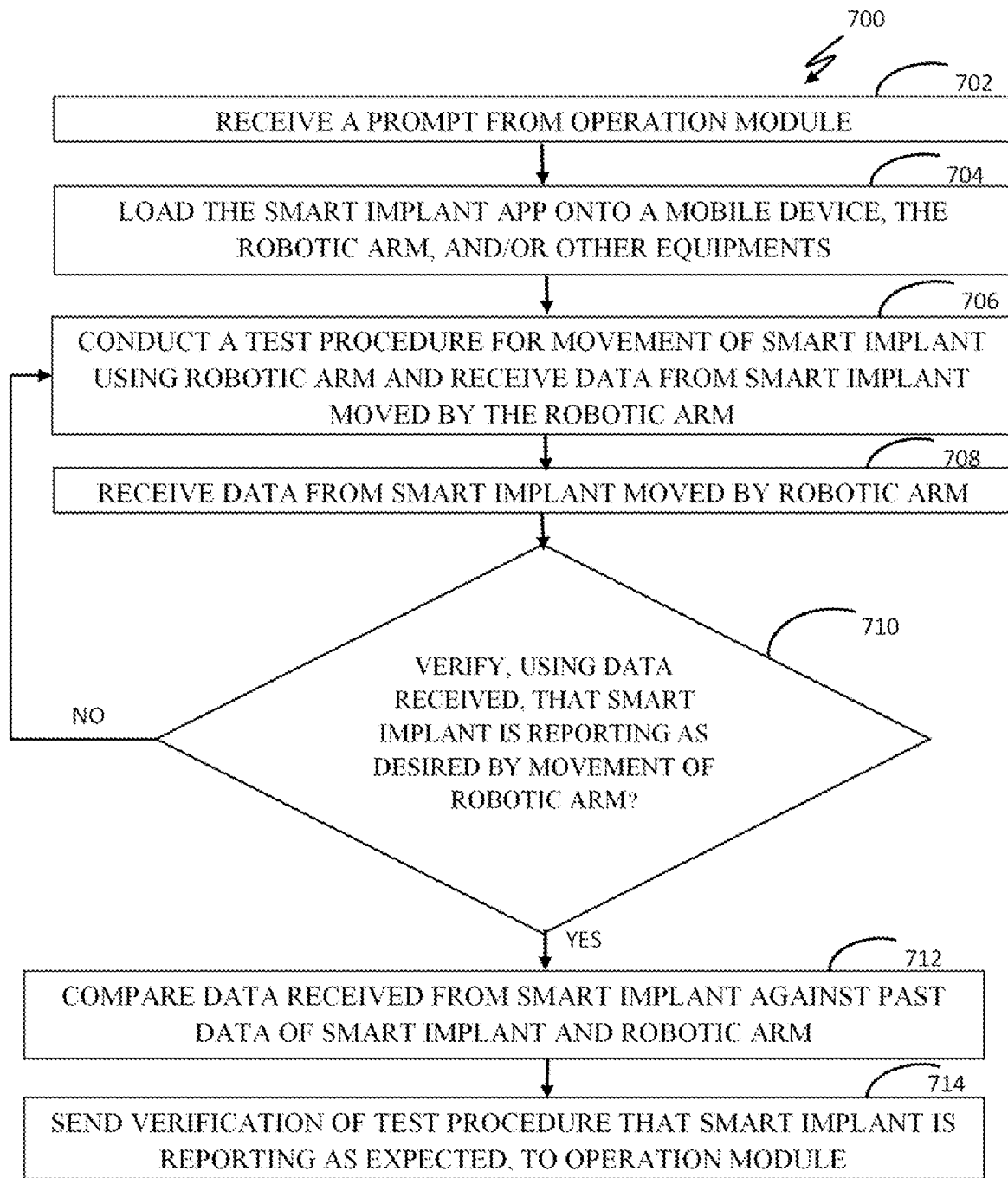
FIG. 7 is a flowchart of a process for operating a testing smart implant module for the robot surgical system.
Figure 8:
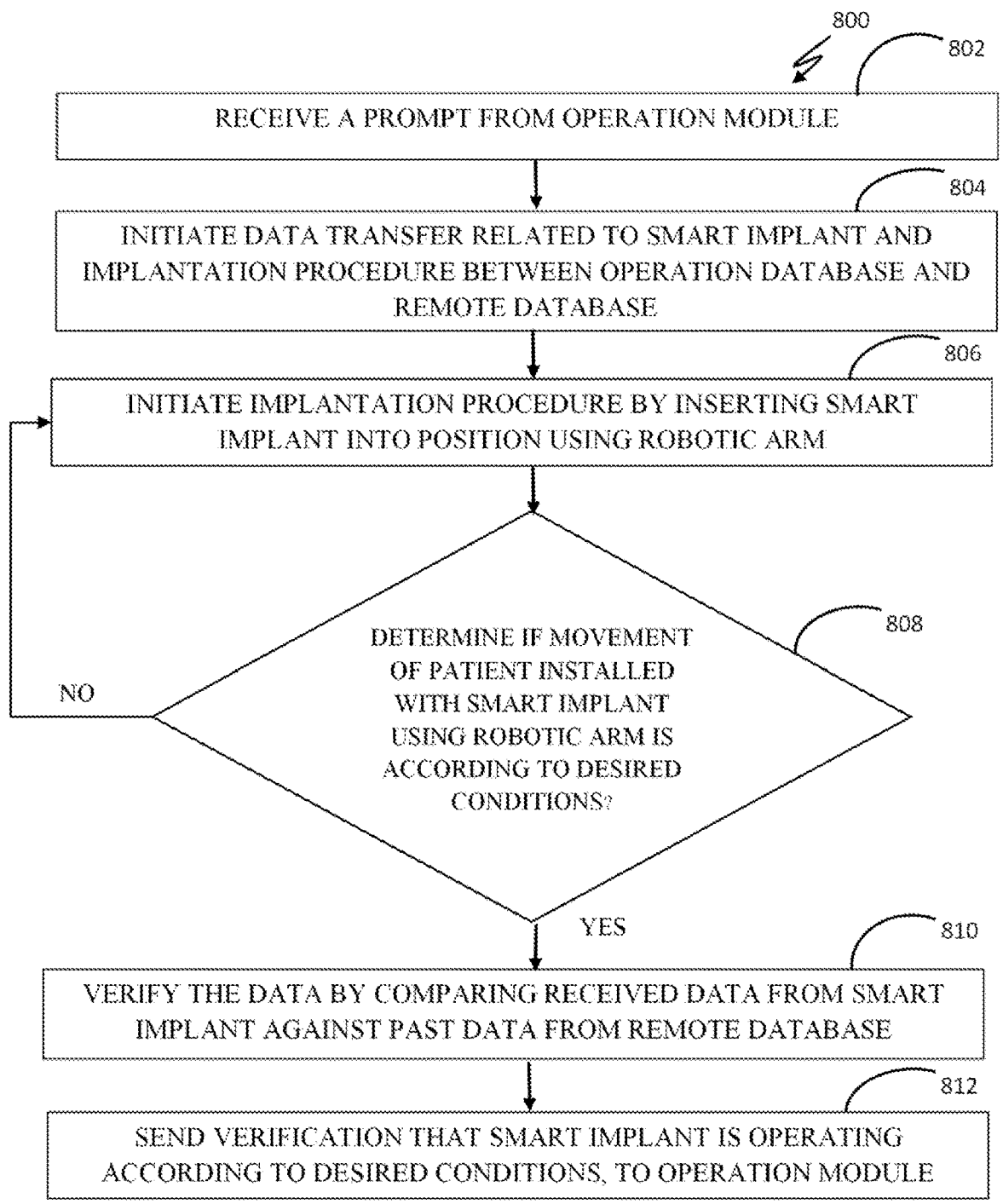
FIG. 8 is a flowchart of a process for operating a workflow module for the robot surgical system.
Figure 9:
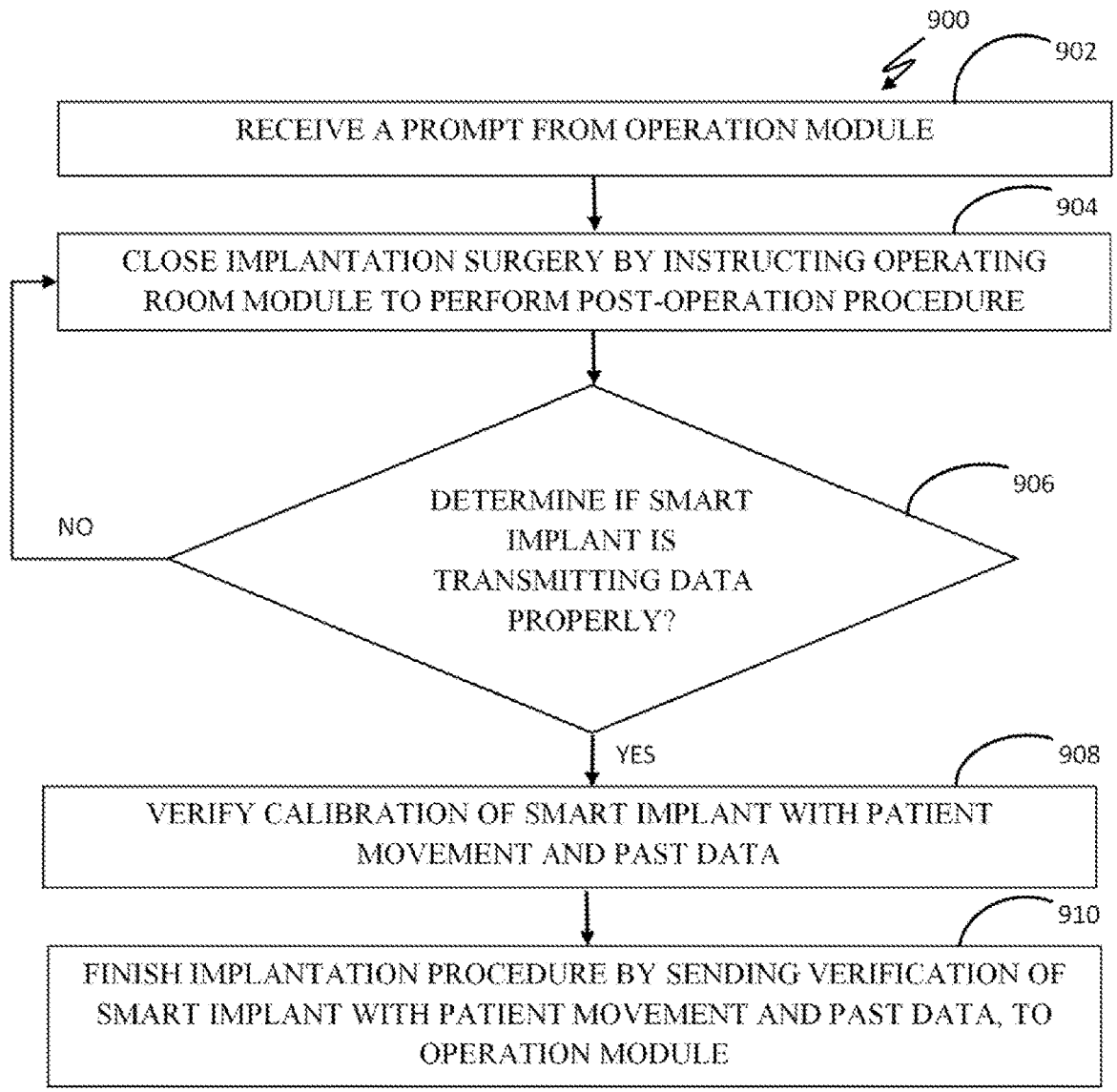
FIG. 9 is a flowchart of a process for operating a control transfer module for the robot surgical system.

Using the data received from the sensors 152A-N (block C) and the received historic data (block B), the computer system 100 can communicate with the smart implant 136 and validate the communication (block D). As described throughout this disclosure, the computer system 100 can test communication before, during, and/or after the surgical procedure. For example, the computer system can perform a pre-surgical validation of the smart implant 136 by generating instructions that, when executed by the robotic arm 134 (block N), cause the robotic arm 134 to move the smart implant 136. Then, the computer system 100 can check whether feedback from the sensors 152A-N indicate expected movements of the smart implant 136 based on movement of the robotic arm 134. Refer to FIG. 7 for additional discussion. The computer system 100 can also perform an intra-surgical validation of the smart implant 136 by monitoring feedback from the sensors 152A-N as the smart implant 136 is placed inside the patient 156 and monitoring the patient 156's conditions. Refer to FIG. 8 for additional discussion. Moreover, the computer system 100 can perform a post-surgical validation of the smart implant 136 as the staff in the operating room 158 go through a closing phase of the surgical procedure. The computer system 100 can iteratively assess feedback from the sensors 152A-N with each step of the closing phase to ensure that, by the time a surgical site is completely closed/stitched up, the smart implant 136 is operating as expected and the patient 156 is experiencing expected conditions. Refer to FIG. 9 for additional discussion.

Moreover, the computer system 100 can output indications about operation (e.g., connection, communication, etc.) of the smart implant 136 in block E. In some implementations, block E can be performed with each validation phase in block D. In some implementations, block E can be performed if the communication/connection of the smart implant 136 cannot be validated in block D. Therefore, a relevant user, such as a surgeon or other staff, can receive real-time feedback before, during, and after the surgical procedure about the smart implant 136 and whether the smart implant 136 is operating correctly.

FIG. 1B illustrates a block diagram of a system 100 for implanting smart implants using robotic telesurgery. The system 100 may include a remote doctor module 102 communicatively coupled to an operating room (OR) module 104 over a network(s) 106. The system 100 can be, for example, a computer system, as shown and described in FIGS. 1A-C.

The OR module 104 can also be in communication via the network(s) 106 to a robot surgical system 150. The remote doctor module 102 and the OR module 104 can be different computer systems. In some implementations, the remote doctor module 102 and the OR module 104 can be different cloud-based services and/or computing systems that can be deployed at user devices, computer systems, or other computing devices. The remote doctor module 102 can be used by a surgeon who is physically remote from a location, such as a hospital or operating room, where a patient is undergoing the surgical procedure (e.g., refer to FIG. 1A). The OR module 104 can be executing in the location where the surgical procedure is being performed by the robot surgical system 150. In some implementations, the OR module 104 and the robot surgical system 150 can be a same system. Moreover, the network 106 can be any type of network that can provide communication (e.g., wired and/or wireless) between the remote doctor module 102, the OR module 104, and the robot surgical system 150.

In some implementations, the system 100 may be referred to as remote robotic surgery or robotic telesurgery that uses AI/ML-based connection tools for remote surgeons to perform surgical procedures involving smart implants. It can be noted that the connection tools may be referred to as a combination of the OR module 104 with AWL-based programmable functions. The smart implants may include, but are not limited to, smart knee implants, smart stent implants, or other smart implants that can be inserted into the patient's body for any duration of time (e.g., permanently, extended periods of time, etc.). In some implementations, components of the system 100, such as the remote doctor module 102 and/or the operating room module 104 may load a software application, app, or cloud-based service that corresponds to a specific smart implant 136 being used in a particular surgical procedure being performed. This application can be used to provide real-time monitoring and operation of components described throughout this disclosure, such as a robotic arm 134 of the robot surgical system 150 and the smart implant 136 itself. Moreover, the system 100 may provide an application store for distributing and using one or more particular integrated modules for the particular surgical procedure being performed. Such an application store may act as a repository of available applications that can be installed and/or deployed at the remote doctor module 102 and/or the operating room module 104, depending on the type of smart implant 136 used and the particular surgical procedure being performed.

As described further below, the smart implant 136 can include sensors 152A-N (e.g., an array of sensors, at least one sensor) and a communication interface 154. The sensors 152A-N can be configured to detect conditions of the smart implant 136 and/or the patient before, during, and after the surgical procedure. The communication interface 154 can provide for communication between the smart implant 136 and the various components described throughout this disclosure.

Still referring to FIG. 1B, the remote doctor module 102 may include a processor 108 for performing any of the operations described herein and for controlling parameters related to the robotic telesurgery (e.g., surgical procedure) being performed. Further, the processor 108 of the remote doctor module 102 may be coupled to a user interface 110 to display parameters related to the smart implant 136, patient conditions, and the robotic telesurgery. It can be noted that the user interface 110 may be a proprietary remote surgery control terminal, smartphone, computer, smart screen, laptop, tablet, or other mobile computing device. Further, the remote doctor module 102 may include a smart implant application integrator module 112 coupled to the processor 108. The smart implant application integrator module 112 may hereinafter be referred to as an app integrator module 112. The app integrator module 112 may allow the surgeon performing the robotic telesurgery to load one or more smart implant applications associated with each smart implant 136 that is being implanted into a patient during the robotic telesurgery. The app integrator module 112 may, in some implementations, be configured to retrieve information related to a particular smart implant 136 from the smart implant application and feed the retrieved information to the user interface 110.

Further, the remote doctor module 102 may include a base module 114 configured to perform operations related to implantation of smart implants using robotic telesurgery. The base module 114 may act as a central module for retrieving and sending information related to the implantation of smart implants. For example, the base module 114 can receive sensor detections from one or more sensor devices in communication with the smart implants and/or the robot surgical system 150. The base module 114 can provide the sensor detections to one or more sub-modules for further processing and generation of control commands for the robotic telesurgery.

Further, the base module 114 may perform operations using one or more sub-modules. For example, the base module 114 may include a pre-operative module 116, an operation module 118, and/or a post-operative module 120. The pre-operative module 116 may be configured to initialize and test the smart implant 136 connection between the operating room module 104 and the remote doctor module 102. The operation module 118 may initiate other modules within the remote doctor module 102 by sending a request to the operating room module 104 related to patient information, doctor data, smart implant type, etc. The post-operative module 120 may be configured to check the communication between the smart implant 136 inside the patient, a remote database 128, and a user device 132. Further, the post-operative module 120 may verify completion of surgical procedure/implantation via the smart implant application at the remote doctor module 102 and may check whether the smart implant 136 is operating properly after implantation. Refer to FIG. 4 for additional discussion about the base module 114 of the remote doctor module 102.

Still referring to FIG. 1B, the remote doctor module 102 may include a communication module 122 configured to be used in parallel with the base module 114 of the remote doctor module 102. The communication module 122 may facilitate establishment of communication between the remote doctor module 102 and the operating room module 104 over the network(s) 106. The communication module 122 may ensure enablement of telesurgery controls between components of the operating room module 104, the robot surgical system 150, and the remote doctor module 102. For example, the communication module 122 may provide smart implant 136 communication control for the remote doctor module 102. It can be noted that the smart implant 136 communication control may facilitate connection with the smart implant 136 to enable control of the smart implant 136, via the robot surgical system 150, during the implantation procedure/surgical procedure. The communication module 122 may be described further in FIG. 11.

The communication module 122 may also include an analytics and reporting module 124 and a smart implant test module 126. The analytics and the reporting module 124 may be configured to collect data from the smart implant 136 and provide alerts over the user interface 110 to the surgeon about the smart implant 136 (e.g., movement/position/orientation of the smart implant 136 inside the patient's body during the robotic telesurgery and/or after the robotic telesurgery). The analytics and reporting module 124 may alert the surgeon when the smart implant 136 may not be moved in a manner as desired or expected for the particular robotic telesurgey, or the smart implant 136 may be moved out of desired parameters during implantation. The analytics and reporting module 124 may provide a detailed analysis of the smart implant 136 via the pre-operative module 116, the operation module 118, and/or the post-operative module 120. The smart implant test module 126 may allow testing of the smart implant 136 using the established connection between the remote doctor module 102 and the operating room module 104 over the network(s) 106 to ensure that communication exists between these components.

Further, the remote doctor module 102 may include a remote database 128 coupled to the processor 108. In some implementations, the remote database 128 can be separate from the remote doctor module 102 and in communication with the module 102 via the network(s) 106. The remote database 128 may store data related to the smart implant 136, patient, and/or robotic telesurgery procedure. The remote database 128 may act as a central database via the network(s) 106, which may include historic data related to previous implants done on one or more patients. The remote database 128 may store a variety of threshold values for each parameter associated with a smart implant 136, including parameters that are measured by sensors during and after the robotic telesurgery, and each vital parameter of a patient.

In an illustrative example, and as shown and described in FIG. 2, the remote database 128 can store information about a patient 1 who is having knee surgery and who will be receiving a smart knee implant. This information can also include a threshold value of range of motion (ROM) for the smart knee implant, which can be within a range of 30° in hyperextension and 180° in flexion extension, with force exerted or loading force of the smart knee implant being within a range of 100 lbs to 500 lbs. This information can vary depending on information about the particular patient, such as their age, height, weight, gender, etc. In another example, a temperature sensor integrated within the smart knee implant can detect a temperature of 35.5 degrees Celsius with a threshold temperature being 36.5 degrees Celsius. An ECG monitoring sensor can detect a heartrate of this particular patient, in beats per minute (bpm), of 82, corresponding to a threshold range of 60-100 bpm. This data can be stored for the patient in the remote database 128. Thus, data that is collected by sensors 152A-N of the smart implant 136 or other sensor systems can be transmitted to the remote database 128 for storage by the pre-operative module 116, the operation module 118, and/or the post-operative module 120 of the remote doctor module 102. In some implementations, the remote database 128 may be storage integrated within a mobile device, a computer system, a portable computer system, a dedicated device, etc.

The OR module 104 may include a processor 130 configured to perform actions related to the implantation of the smart implants in real-time by communicating with the base module 114 of the remote doctor module 102. It can be noted that an operating room (OR) may be at a surgical facility where the patient is undergoing the robotic telesurgery. Further, the OR module 104 may include the user device 132, which can be configured to receive data related to the operation of the smart implant 136 (e.g., post-operatively). The user device 132 may include, but is not limited to, a mobile phone, smart phone, computer system, laptop, tablet, or other computing device. The user device 132 may be used by the patient who undergoes the robotic telesurgery. The patient may, for example, view information presented at the user device 132 to determine whether their implant is properly implanted within their body.

The OR module 104 may communicate with the robot surgical system 150, which can include at least one robotic arm 134. The robotic arm 134 may be controlled by AI/ML techniques. The robotic arm 134 may be used for carrying out desired effects or performing specific actions during the robotic telesurgery, such as modifying or implanting smart implants such as knee implants, stents, cochlear implants, etc. Such AI/ML-controlled robotic surgery equipment may facilitate staff, such as a nurse, located at the OR to perform the procedure by receiving guidelines and directions (e.g., control commands) from the surgeon at the remote doctor module 102.

Further, the OR module 104 can communicate with the smart implant 136. It can be noted that the smart implant 136 may be gripped by the robotic arm 134 during the robotic telesurgery to be placed into the patient. The smart implant 136 may be oriented according to an orientation of the robotic arm 134. It can be noted that the orientation of the smart implant 136 may be in Cartesian coordinates along X, Y, Z coordinates. Further, the smart implant 136 may include one or more sensors 152A-N integrated within the smart implant 136 to continuously monitor the operation of the smart implant 136 within the patient. It can be noted that the smart implant 136 may be communicatively coupled with the smart implant application at the remote doctor module 102 to monitor parameters detected from the sensors 152A-N of the smart implant 136.

The smart implant 136 may send data from the sensors 152A-N within the patient to the smart implant application, so that the surgeon may continuously monitor the operation of the smart implant 136 and may also monitor recovery of the patient after the robotic telesurgery, remotely. The sensors 152A-N may include, but are not limited to, temperature sensors, motion sensors, transducers, heart rate (ECG) monitoring sensors/devices, etc. In some implementations, the smart implant 136 may be integrated with motion sensors such as accelerometers, tilt sensors, etc. to determine orientation of the smart implant 136 when implanted during the robotic telesurgery.

Moreover, referring to the robot surgical system 150, the robotic arm 134 can be a type of mechanical arm, AI/ML programmable, that can perform surgical procedures with more precision, flexibility, and control than with conventional, non-robotic techniques. The robotic arm 134 may be part of a more complex robot. The robotic arm 134 may be a Cartesian robot, a collaborative robot, an anthropomorphic robot, a SCARA robot, a spherical/polar robot, an articulated robot, or a parallel robot, without departing from the scope of the disclosure. Moreover, as described herein, the robotic arm 134 can be part of a surgical robot, such as the robot surgical system 150.

Referring back to the OR module 104, the module 104 may also include a base module 138 coupled to the processor 130 and configured to facilitate the operation of the robotic arm 134 during the robotic telesurgery. The base module 138 can retrieve information related to the smart implant 136 from the remote database 128. The base module 138 of the OR module 104 may initialize operation of the robotic arm 134 to perform the robotic telesurgery by establishing a connection between the OR module 104 and the remote doctor module 102. Further, the OR module 104 may include a telesurgery module 140 coupled to the processor 130. The telesurgery module 140 may be configured to receive instructions from the remote doctor module 102 during the robotic telesurgery, such as instructions (e.g., control commands) for the robotic arm 134 such that the robotic arm 134 can precisely and accurately perform actions relating to implanting the smart implant 136 into the patient in the OR.

The OR module 104 may also include an operation database 142 coupled to the processor 130. In some implementations, the operation database 142 can be separate from the OR module 104. Moreover, in some implementations, the operation database 142 can be the same as the remote database 128. The operation database 142 may store information such as, but not limited to, implantation surgery (e.g., robotic telesurgery), robotic arm 134 orientation and other position data, patient identification, patient stability conditions during the implantation surgery, monitoring equipment, etc. The operation database 142 may continuously synchronize data related to the robotic telesurgery with the remote database 128.

Further, the OR module 104 may include a communication interface 144 to maintain connection with the remote doctor module 102 and/or the robot surgical system 150 in real-time, over the network(s) 106. The communication interface 144 may facilitate synchronization of data between the operation database 142 of the OR module 104 and the remote database 128 of the remote doctor module 102.

The operation database 142 is described in further detail with regards to FIG. 3. For example, as shown in FIG. 3, the operation database 142 can store information that a patient named Alex is undergoing a robotic telesurgery to replace a traditional knee implant with a smart knee implant. It can be noted that periodic monitoring can 5 milliseconds (ms). At 12:22:10 PM, Alex had a detected blood pressure of 105/85 and a heartrate of 80 bpm, with an orientation of the smart knee implant at 13 cm, 12 cm, 14 cm with respect to origin. In another example, the operation database 142 also stores information indicating that at 12:22:20 PM, Alex's heartrate raised from 80 bpm to 89 bpm, corresponding to his blood pressure rise to 120/90. The information stored in the operation database 142 can then be used to determine how the robotic telesurgery is being performed and to monitor the patient's conditions to determine whether the patient is safe and healthy. If changes in the monitored conditions of the patient appear out of predetermined threshold ranges, for example, the remote doctor module 102 may determine one or more adjustments to the robotic telesurgery that can be performed to improve the patient's conditions.

The network(s) 106 may be implemented using a collection of server devices to provide one or more services to coupled devices, including but not limited to the remote doctor module 102, the OR module 104, and the robot surgical system 150. The network(s) 106 may be a wired and/or a wireless network. The network(s) 106, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques, known in the art. The network(s) 106 may allow ubiquitous access to shared pools of configurable resources and higher-level services that can be rapidly provisioned with minimal management effort, often over the internet, and relies on sharing of resources to achieve coherence and economies of scale, like a public utility, while third-party clouds enable organizations to focus on their core businesses instead of expending resources on computer infrastructure and maintenance. The network(s) 106 may also be synchronized with the remote database 128 and/or an operation database 142 of the OR module 104, to store information associated with the smart implant as well as data related to the robotic telesurgery procedure.

FIG. 1C is a state flow diagram for performing a surgical procedure using the disclosed techniques. As shown and described throughout this disclosure, the computer system 100 can establish connection (e.g., communication) with the robotic arm 134 and the smart implant 136 at state 0. If connection is successfully established in state 0, the computer system 100 can proceed to state 1.

Next, in state 1, the computer system 100 can perform pre-surgical validation of the smart implant 136 by controlling movement of the robotic arm 134 and verifying feedback from the smart implant 136 (refer to FIG. 7). If validation is successful in state 1, the computer system 100 can proceed to state 2.

Next, in state 2, the computer system 100 can perform intra-surgical validation of the smart implant 136 by verifying feedback from the smart implant 136 and patient parameters (refer to FIG. 8). If validation is successful in state 2, the computer system 100 can proceed to state 3.

Next, in state 3, the computer system 100 can perform post-surgical validation of the smart implant 136 by verifying feedback from the smart implant 136 at each phase of closing the surgical procedure (refer to FIG. 9). If validation is successful in state 3 (e.g., once a practitioner begins stitching up the surgical site, once the surgical site is nearly all stitched up, once the surgical site is completely stitched up, once the patient is removed from anesthesia, once the patient wakes up, etc.), the computer system 100 can stop performing the validation techniques described herein. In other words, if validation is successful in state 3, the computer system 100 can determine that the smart implant 136 is operating as expected and/or the patient is safe/healthy.

If, during execution of any of the states, validation fails, the computer system 100 can continue to test connection with the smart implant 136 and/or the robotic arm 134. Any state failure can indicate to a surgical team that other and/or additional medical intervention is needed. In some implementations, when validation fails, the workflow of the procedure may be halted, thereby causing the surgical team to respond appropriately to the warning. In some implementations when validation fails, the computer system 100 can generate one or more suggested interventions that the surgical team can implement. The interventions can be determined using one or more AI and/or ML techniques described herein.

FIG. 4 is a flowchart of a process 400 for operating a base module of the remote doctor module described herein (e.g. the base module 114 in FIG. 1B). FIG. 4 is explained in conjunction with FIGS. 1A-C, FIG. 2, FIG. 3, FIG. 5, FIGS. 6A-B, FIG. 7, FIG. 8, FIG. 9, FIG. 10, FIG. 11, FIG. 12, and FIG. 13. It should also be noted that in some implementations, one or more blocks in the process 400 may occur in one or more different orders. For example, two blocks shown in succession in the process 400 may in fact be executed substantially concurrently in the reverse order, depending upon the functionality involved. In addition, the blocks described herein can be understood as representing decisions made by a hardware structure, such as a state machine. The process 400 can be performed by the remote doctor module 102. One or more blocks in the process 400 can also be performed by one or more other computer systems, computing devices, services, cloud-based systems, and/or cloud-based services. For illustrative purposes, the process 400 is described from the perspective of the base module 114.

For example, as described throughout this disclosure, the remote doctor module 102 may perform actions related to implantation of the smart implant 136 using the base module 114 (refer to FIGS. 1A-C). More particularly, the operation module 118 of the base module 114 may include one or more sub-modules to perform actions relating to implantation of the smart implant 136. The sub-modules may include, but are not limited to, a testing smart implant module, a workflow module, and a control transfer module, which may be described in conjunction with the operation module 118. Operation of these sub-modules are described in the process 400.

Referring to the process 400, the base module 114 may receive a request from a surgical facility to schedule a robotic telesurgery implantation procedure (block 402). The request can be received from a computing device at the surgical facility. For example, for patient Alex, who is being operated in a surgical facility in New York, and is operated via telesurgery procedure being conducted by Dr. Tim, who performs the telesurgery remotely from San Francisco, the base module 114 can receive a request from the surgical facility in New York to schedule the telesurgery implantation procedure for Alex.

Once the robotic telesurgery is scheduled, the base module 114 may establish communication between the OR module 104 and the remote doctor module 102 over the network(s) 106, using the communication module 122 (block 404). It can be noted that the communication module 122 may perform actions related to facilitation of communication between the OR module 104 and the remote doctor module 102, in parallel with the base module 114. For example, the base module 114 can establish a connection via the network(s) 106 between a computing device used by Dr. Tim, such as the remote doctor module 102, with the OR module 104 that is used by staff at the OR where Alex's surgery is being performed.

Once communication is established, the base module 114 may trigger the pre-operative module 116, at block 406. The pre-operative module 116 may facilitate establishment of a connection between the robotic arm 134, the smart implant 136, and the remote doctor module 102 such that the robotic arm 134 can be prepared to begin the robotic telesurgery with the smart implant 136. The pre-operative module 116 is further described in FIG. 5.

Successively, the base module 114 may receive confirmation of connection between the smart implant 136 and the remote doctor module 102, at block 408. For example, the base module 114 can receive an indication that a smart knee implant is exchanging data with the remote doctor module 102 with an upload speed of 50 Mb/sec and a download speed of 25 Mb/sec.

The base module 114 may trigger the operation module 118, at block 410 once the connection is confirmed. The operation module 118 is described further in FIGS. 6A-B. The operation module 118 may perform functions related to implantation of the smart implant 136 using one or more sub-modules, which may include, a testing smart implant module, workflow module, control transfer module, etc.

In block 412, the base module 114 may continuously receive verification of the smart implant 136 with patient movement and historic data from the operation module 118. For example, the base module 114 can receive an indication (e.g., from one or more sensors of the smart implant) that the smart knee implant implanted on the left leg of Alex is having a ROM of 30° to 150°, which is within a threshold range of 30° to 180° between a flexion extension and hypertension, and the force exerted by the smart knee implant can be measured as 250 lbs, which can be according to desired conditions as verified from historic data (e.g., refer to FIG. 3).

Next, the base module 114 may trigger the post-operative module 120, at block 414. The operation of the post-operative module 120 is described further in FIG. 10.

The base module 114 may periodically (e.g., at predetermined times, randomly, continuously, etc.) receive data related to the smart implant 136 from the post-operative module 120, at block 416. For example, the base module 114 can receive data relating to the smart knee implant's temperature and forced exerted by the smart knee implant at different times after Alex's robotic telesurgery. The data may be temporarily saved to local memory of the implant 136 until it can be transmitted to the base module 114.

Further, the base module 114 may send the received data to the operation database 142 and/or the remote database 128, at block 418. The smart knee implant, with a plurality of sensors integrated within, can continuously send data to the smart implant application of the remote doctor module 102, which can then be used by the surgeon to monitor Alex's conditions and effectiveness of the smart knee implant.

Figure 5:
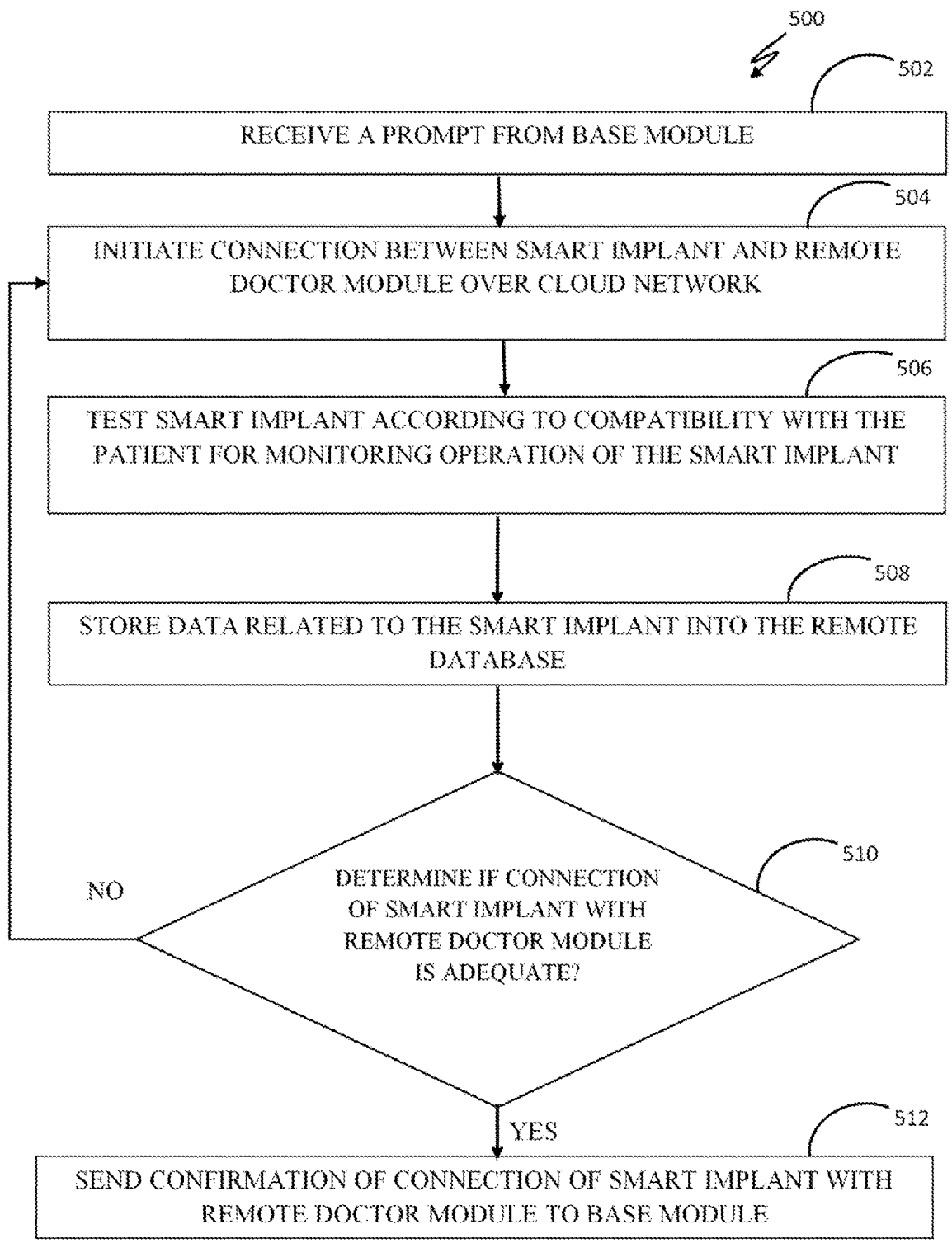
FIG. 5 is a flowchart of a process for operating a pre-operative module for the robot surgical system described herein.

FIG. 5 is a flowchart of a process 500 for operating a pre-operative module for the robot surgical system described herein (e.g., the pre-operative module 116 of FIG. 1B). The process 500 can be performed to ensure proper connection between components that are used to perform the robotic telesurgery. Once connection is established, the robotic telesurgery can begin. It should also be noted that in some implementations, one or more blocks in the process 500 may occur in one or more different orders. For example, two blocks shown in succession in the process 500 may in fact be executed substantially concurrently in the reverse order, depending upon the functionality involved. In addition, the blocks described herein can be understood as representing decisions made by a hardware structure, such as a state machine. The process 500 can be performed by the remote doctor module 102. One or more blocks in the process 500 can also be performed by one or more other computer systems, computing devices, services, cloud-based systems, and/or cloud-based services. For illustrative purposes, the process 500 is described from the perspective of the pre-operative module 116.

Referring to the process 500 in FIG. 5, the pre-operative module 116 may receive a prompt from the base module 114, at block 502. The pre-operative module 116 may be configured to establish communication between the remote doctor module 102 and the OR module 104. The pre-operative module 116 may therefore test a connection between the remote doctor module 102 and the OR module 104, and then may receive a reply from the OR module 104 that the communication is established. Further, the pre-operative module 116 may initiate a connection between the smart implant 136 and the remote doctor module 102 over the network(s) 106, at block 504. The pre-operative module 116 may initiate the connection of the smart implant 136 to check whether the sensors 152A-N of the smart implant 136 have proper connection with the smart implant 136.

The pre-operative module 116 may also test the smart implant 136 according to compatibility with the patient for monitoring operation of the smart implant 136, at block 506. The pre-operative module 116 may check the smart implant 136 against one or more parameters to determine compatibility of the smart implant 136 for the patient (e.g., whether the appropriate smart implant 136 has been selected for the particular patient's conditions). The parameters may include, but are not limited to, the patient's ROM, orientation of the smart implant 136, amount of force exerted by the smart implant 136, and/or speed of the smart implant 136 with a corresponding minimum and maximum speed at which the smart implant 136 is implanted inside the patient's body. The ROM may be measured by an angular movement of the smart implant 136 as it is expected to enter the patient's body. The ROM of the smart implant 136 may also be measured by a common goniometer. For example, the pre-operative module 116 can test that a smart knee implant has a ROM between 0° to 150°, with 100 pounds (lbs) of force exerted by the smart knee implant to withstand. The pre-operative module 116 may also check that the ROM of 0° to 150° is uploaded from the smart knee implant to the smart implant application so that the surgeon can view this information at the remote doctor module 102 before beginning the robotic telesurgery.

In block 508, the pre-operative module 116 may store data related to the smart implant 136 into the remote database 128. The pre-operative module 116 may also retrieve data related to the smart implant 136 from the operation database 142 and may update the remote database 128 at the remote doctor module 102 based on the retrieved data. For example, the pre-operative module 116 can store data that the smart knee implant has the ROM between 0° to 150° between normal flexion extension and hyperextension, and the force exerted by the smart knee implant to withstand is 100 lbs. The pre-operative module 116 may also store information indicating that the smart knee implant is to be implanted on a left leg of Alex. This information can then be retrieved by the remote doctor module 102, from the remote database 128, and used by the surgeon during the robotic telesurgery.

The pre-operative module 116 may then determine if the connection of the smart implant 136 with the remote doctor module 102 is adequate, at block 510. In other words, the pre-operative module 116, after initiating a connection between the smart implant 136 and the remote doctor module 102, may determine whether the connection between the smart implant 136, the processor 108 of the remote doctor module 102, and the processor 130 of the OR module 104 is securely established. The connection may be measured by a data transmission rate of transmission between the smart implant 136 and the remote doctor module 102.

Sometimes, the pre-operative module 116 may determine that the connection between the smart implant 136 and the remote doctor module 102 is insufficient in block 510. Thus, the pre-operative module 116 can return to block 504 and repeat blocks 504-508 until a sufficient connection is established and thus the robotic telesurgery can begin. For example, the pre-operative module 116 can determine that the remote doctor module 102 is not receiving data from the smart knee implant and the data transmission rate is 0 megabytes per second (MB/S). In this case, the pre-operative module 116 may be redirected back to block 504 to again initiate the connection of the smart implant 136 and the remote doctor module 102.

Other times, the pre-operative module 116 may determine that the connection between the smart implant 136 and the remote doctor module 102 is adequate/sufficient in block 510. The connection between the smart implant 136 and the remote doctor module 102 may be determined by the data transmission rate. An adequate/sufficient data transmission rate may be within a range of 10 MB/S to 50 MB/PS to ensure smooth transfer of data. One or more other ranges of data transmission rates may also be used in block 510.

As an illustrative example, the pre-operative module 116 can determine that the remote doctor module 102 receives data from the smart knee implant with a data transmission rate of 10 MB/S, above a predetermined threshold value of 8 MB/S, for smooth transfer of data. In this case, the pre-operative module 116 can proceed to block 512, to send confirmation of the connection between the smart implant 136 and the remote doctor module 102 to the base module 114. For example, confirmation can include information about the smart implant 136, such as information indicating that the smart knee implant has the ROM of 0° to 150° between normal flexion extension and hyperextension, and the force exerted by the smart knee implant to withstand is 100 lbs.

Figure 6A:
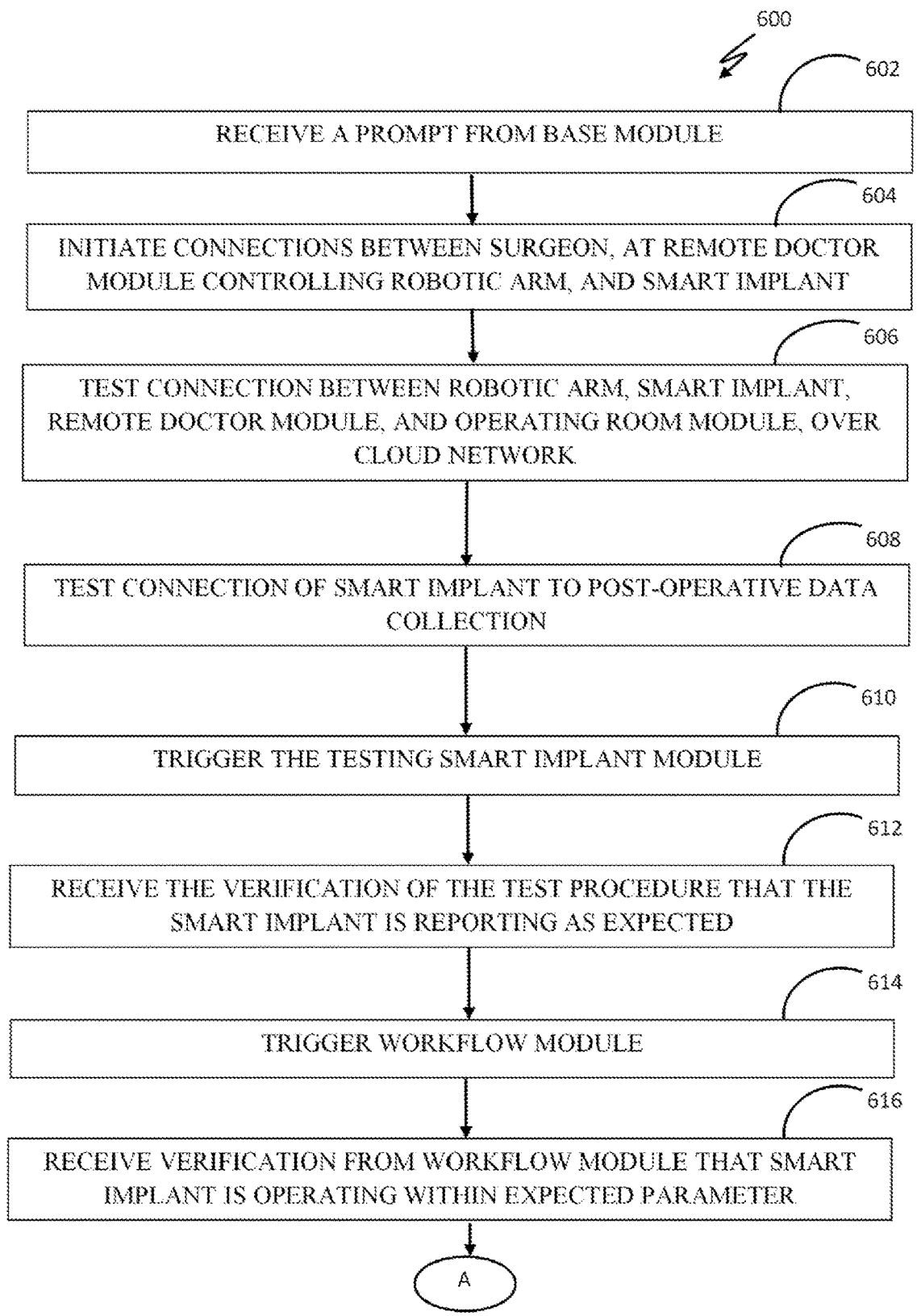
FIGS. 6A-B is a flowchart of a process for operating an initiation module for the robot surgical system described herein.
Figure 6B:
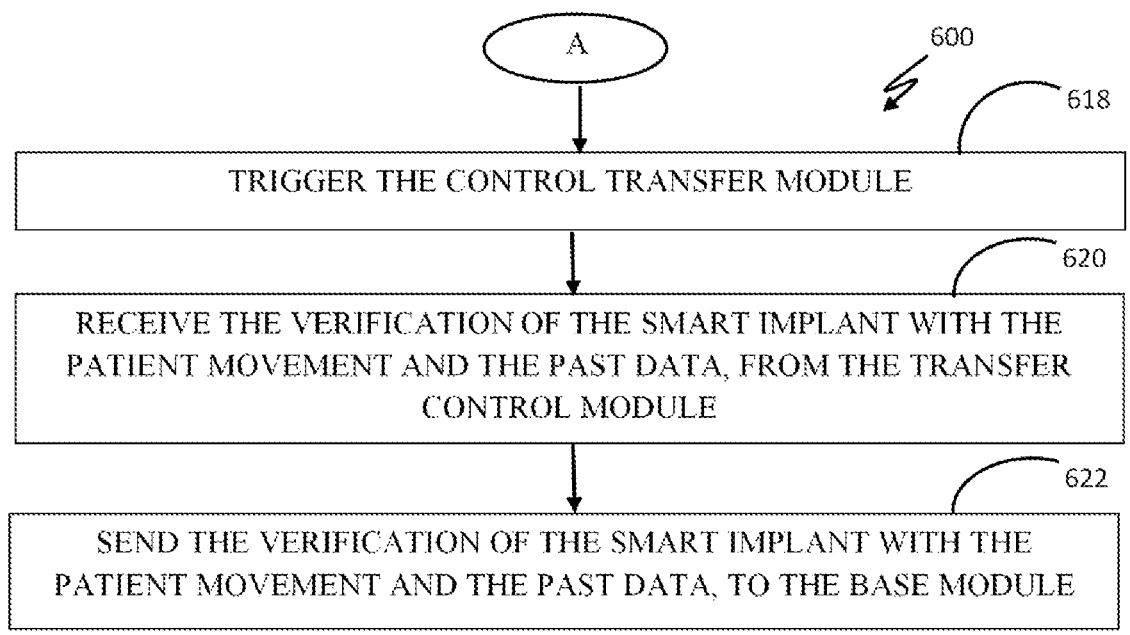

FIGS. 6A-B is a flowchart of a process 600 for operating an initiation module for the robot surgical system described herein. It should also be noted that in some implementations, one or more blocks in the process 600 may occur in one or more different orders. For example, two blocks shown in succession in the process 600 may in fact be executed substantially concurrently in the reverse order, depending upon the functionality involved. In addition, the blocks described herein can be understood as representing decisions made by a hardware structure, such as a state machine. The process 600 can be performed by the remote doctor module 102. One or more blocks in the process 600 can also be performed by one or more other computer systems, computing devices, services, cloud-based systems, and/or cloud-based services. For illustrative purposes, the process 600 is described from the perspective of the operation module 118.

Referring to the process 600 in both FIGS. 6A-B, the operation module 118 may receive a prompt from the base module 114, at block 602. The prompt can indicate that a stable connection has been established between components for the robotic telesurgery and that the robotic telesurgery can begin. The stable connection can be established and confirmed using a handshake process with sensors of the robotic arm 134. For example, each servo in the robotic arm 134 can provide state data to the base module 114, which can also be used by the computer system 100 to geometrically derive position and orientation of the robotic arm 134. In some implementations, a visual system, such as an imaging device or medical imaging system, can be used to determine that the stable connection has been established and/or the position and orientation of the robotic arm 134. Accordingly, the operation module 118 may perform functions related to implanting the smart implant 136 in the patient's body by instructing the robotic arm 134 of the robot surgical system 150 to mount the smart implant 136. The operation module 118 may control orientation and positioning of the robotic arm 134 to move the smart implant 136.

The operation module 118 may initiate connections between the surgeon, at the remote doctor module 102 controlling the robotic arm 134, and the smart implant 136, at block 604. For example, the operation module 118 may request information from the OR module 104, such as patient information, type of smart implant to be implanted in the patient, staff requirements, etc. This information can be used to ensure that the robotic telesurgery is ready to be performed. This information can also be transmitted between components to test the connection. The operation module 118 may initiate that the patient has a heartrate of 85 bpm, blood pressure of 105/85, and will be receiving a knee implant with ROM of 165° and a maximum operating load or maximum force exerted by the smart knee implant of 500 lbs.

The operation module 118 may test the connection between the robotic arm 134, the smart implant 136, the remote doctor module 102, and the OR module 104, over the network(s) 106, at block 606. For example, the operation module 118 can transmit the information mentioned above to one or more of the components 134, 136, 102, and/or 104 to determine whether they have a stable and adequate connection. In other words, the operation module 118 may check whether the robotic arm 134 and the smart implant 136 have a secure connection with the surgeon at the remote doctor module 102. For example, the operation module 118 may instruct the robotic arm 134 to move from a 12 cm, 14 cm, 13 cm orientation/position to a 10 cm, 12 cm, 12 cm, such as moving 2 cm along an x-axis. The operation module 118 can then verify that the smart implant 136 is oriented from 10 cm, 10 cm, 10 cm to 12 cm, 10 cm, 10 cm. If the smart implant 136 is oriented as such, then the operation module 118 can very a secure connection. Alternatively, the smart implant 136 may be moved, and data may be received from the smart implant 136 indicating it's second orientation. The operation module 118 can then confirm the second orientation of the smart implant 136 with the instructed movement of the robotic arm 134 to determine that a secure connection has been established.

The operation module 118 may also test the connection of the smart implant 136 to post-operative data collection, at block 608. The operation module 118 may check the connection of the smart implant 136 with the post-operative data collection to load data related to the robotic telesurgery. The post-operative data collection may include, but is not limited to, a mobile device, cloud-based system/service, a computer system, a data store or database, and/or one or more other devices for data collection. For example, the operation module 118 can test the connection of a smart knee implant with a mobile device so that after the robotic telesurgery is complete, data, such as, range of motion and loading forces from the smart knee implant, can be transmitted smoothly from sensors of the smart knee implant to the mobile device.

The operation module 118 may trigger a testing smart implant module, at block 610. The testing smart implant module is described further in FIG. 7.

The operation module 118 may also receive a verification from a test procedure indicating that the smart implant 136 is reporting as expected, at block 612. For example, the operation module 118 can receive an indication that the orientation of the smart knee implant has been changed from 10 cm, 10 cm, 10 cm, to 12 cm, 12 cm, 11 cm, and that the ROM of the smart knee implant has been changed from 30° to 150° from normal flexion extension to hyperextension and that the force exerted by the smart knee implant is 120 lbs. Receiving this verification can further indicate that stable connection is established.

Moreover, the operation module 118 may trigger a workflow module, at block 614. The operation of the workflow module is described further in FIG. 8.

The operation module 118 may receive verification from the workflow module that the smart implant is operating within expected parameters, at block 616. For example, the operation module 118 can receive an indication from the workflow module that the smart knee implant was implanted on the left leg of Alex having the ROM of 30° to 150°, which is within the predetermined threshold range of 30° to 180° between the flexion extension and the hypertension, and the force exerted by the smart knee implant is 250 lbs, which is according to desired conditions of smart knee implant as verified from historic data.

The operation module 118 may trigger a control transfer module, at block 618. The operation of the control transfer module is described further in FIG. 9.

Next, the operation module 118 may receive verification from the smart implant 136 that includes patient movement data as well as historic data from a transfer control module, at block 620. Accordingly, the operation module 118 may send a verification of the smart implant 136 with the patient movement and the historic data to the base module 114, at block 622. For example, the operation module 118 can send a verification that when Alex moves his left leg between the ROM of 30° to 50°, the smart knee implant can have the ROM of 30° to 45°, which can be less 5° less than the expected ROM with respect to the rest of Alex's left leg. This information can be used by the surgeon to determine one or more treatment options and/or changes to make to Alex's robotic telesurgery and/or his treatment after the robotic telesurgery.

FIG. 7 is a flowchart of a process 700 for operating a testing smart implant module for the robot surgical system. It should also be noted that in some implementations, one or more blocks in the process 700 may occur in one or more different orders. For example, two blocks shown in succession in the process 700 may in fact be executed substantially concurrently in the reverse order, depending upon the functionality involved. In addition, the blocks described herein can be understood as representing decisions made by a hardware structure, such as a state machine. The process 700 can be performed by one or more sub-modules of the remote doctor module 102. One or more blocks in the process 700 can also be performed by one or more other computer systems, computing devices, services, cloud-based systems, and/or cloud-based services. For illustrative purposes, the process 700 is described from the perspective of a testing smart implant module.

Referring to the process 700 in FIG. 7, the testing smart implant module may receive a prompt from the operation module 118, at block 702. The testing smart implant module may be configured to conduct test procedures on the smart implant 136 using the robotic arm 134 from the remote doctor module 102.

In block 704, the testing smart implant module may load the smart implant application onto a mobile device, the robotic arm 134, or other equipment used by the staff and/or surgeon during the robotic telesurgery.

Since the smart implant application may be configured to communicate with the smart implant 136, the testing smart implant module may conduct a test procedure for movement of the smart implant 136 using the robotic arm 134, at block 706. Testing the movement can include generating instructions that cause the robotic arm 134 to change its orientation, which, in return, should change the ROM of the smart implant 136. As an illustrative example, the testing smart implant module can generate instructions causing the robotic arm 134 to changes its orientation of 14 cm, 11 cm, 10 cm to 12 cm, 11 cm, 13 cm. If the module receives sensors readings from the smart knee implant indicating that the orientation of the smart knee implant changed from 10 cm, 10 cm, 10 cm, to 12 cm, 12 cm, 11 cm and that the ROM of the smart knee implant changed from 30° hyperextension to 150° flexion extension, the module can determine that the smart implant 136 is being accurately and appropriately moved by the robotic arm 134.

Accordingly, the testing smart implant module may receive data from the smart implant 136 that is being moved by the robotic arm 134, at block 708. As mentioned above, the data can be received from sensors of the smart implant 136 (e.g., the sensors 152A-N). The testing smart implant module can continuously receive the data while the smart implant 136 is being moved in real-time.

Next, the testing smart implant module may verify, using the data received, that the smart implant 136 is reporting as desired by the movement of the robotic arm 134, at block 710. Sometimes, the testing smart implant module may determine that the smart implant 136 is not reporting according to conditions as desired by manipulating orientation of the robotic arm 134. For example, the testing smart implant module can determine, based on the received data, that when the orientation of the robotic arm 134 is changed from 14 cm, 11 cm, 10 cm to 12 cm, 11 cm, 13 cm, the orientation of the smart knee implant changes from 10 cm, 10 cm, 10 cm, to 12 cm, 12 cm, 11 cm, and the ROM of the smart knee implant is changed from 0° to 15° from normal flexion extension to hyperextension. The module can determine that these changes in movement of the smart knee implant are not in accordance with threshold parameters (e.g., the historic data described throughout this disclosure), such as a threshold ROM range of 30° hyperextension to 180° flexion extension. In this case, the testing smart implant module may return to block 706 to conduct the test procedure for movement of the smart implant 136 using the robotic arm 134 and repeat the blocks 706-720 until smart implant 136 movement is accurate/within threshold parameters.

Sometimes, the testing smart implant module may verify that the smart implant 136 is operating according to conditions as desired by manipulation of the robotic arm 134 in block 710. In this case, the testing smart implant module may proceed to block 712 to compare data received from the smart implant 136 with historic data about the smart implant 136 and the robotic arm 134. This historic data can be retrieved from the remote database 128. Comparing the data in block 712 allows the testing smart implant module to determine whether the smart knee implant is accurately changing in movement whenever moved by the robotic arm 134. In some implementations, block 712 can be performed as part of the determination in block 710.

As an illustrative example, the testing smart implant module can retrieve data stored in the remote database 128 indicating that orientation of the robotic arm 134 is changed from 14 cm, 11 cm, 10 cm to 12 cm, 11 cm, 13 cm, which causes the orientation of the smart knee implant to change from 10 cm, 10 cm, 10 cm, to 12 cm, 12 cm, 11 cm and the ROM of the smart knee implant to change from 40° to 170° from normal flexion extension to hyperextension (which is in accordance with the threshold ROM range of 30° hyperextension to 180° flexion extension) while the force exerted by the smart knee implant to fall between 100 lbs to 500 lbs. The testing smart implant module can compare this received data to the real-time data received from the sensors 152A-N of the smart knee implant indicating that when the orientation of the robotic arm 134 is manipulated from 14 cm, 11 cm, 10 cm to 12 cm, 11 cm, 13 cm, the ROM of the smart knee implant is changed from 30° to 150° from normal flexion extension to hyperextension with force exerted by the smart knee implant at 120 lbs. Since the real-time data is similar to or otherwise falls within ranges of the retrieved data, the testing smart implant module can verify that the smart knee implant's movement is accurately changing according to desired conditions when controlled by the robotic arm 134.

Finally, the testing smart implant module may send verification from the test procedure that the smart implant 136 is reporting as expected, to the operation module 118, at block 716. As a result, the smart implant 136 can be manipulated, by the operation module 118, during the robotic telesurgery.

FIG. 8 is a flowchart of a process 800 for operating a workflow module for the robot surgical system. It should also be noted that in some implementations, one or more blocks in the process 800 may occur in one or more different orders. For example, two blocks shown in succession in the process 800 may in fact be executed substantially concurrently in the reverse order, depending upon the functionality involved. In addition, the blocks described herein can be understood as representing decisions made by a hardware structure, such as a state machine. The process 800 can be performed by the remote doctor module 102. One or more blocks in the process 800 can also be performed by one or more other computer systems, computing devices, services, cloud-based systems, and/or cloud-based services. For illustrative purposes, the process 800 is described from the perspective of the a workflow module, which may be a sub-module of the operation module 118.

The workflow module may receive a prompt from the operation module 118, at block 802, to function during the robotic telesurgery. The prompt can indicate that the workflow module is ready to perform its functions during the robotic telesurgery.

Thus, the workflow module may initiate data transfer related to the smart implant 136 during the robotic telesurgery between the operation database 142 and the remote database 128, at block 804.

The workflow module may also initiate the robotic telesurgery by generating instructions that, when executed, cause the robotic arm 134 to put the smart implant 136 into a position necessary for implanting the smart implant 136 in the patient's body, at block 806. For example, the workflow module may generate instructions that position the robotic arm 134 at a specific position for the smart implant 136 to be accurately implanted into a particular region of the patient's body. In some implementations, the workflow module may also generate instructions that cause a second robotic arm 134 (or staff in the OR) to secure the smart implant 136 to the patient by inserting one or more screws that can attach the smart implant 136 to one or more bones of the patient. Alternatively, the workflow module can generate instructions indicating that the smart implant 136 should be clamped in place to a particular portion of the patient's body for a temporary connection.

Successively, the workflow module may determine if movement of the patient having the smart implant 136 installed by the robotic arm 134 is within expected parameters, at block 808. The parameters can be retrieved from the remote database 128 in block 804. Sometimes, the workflow module may determine the movement of the smart implant 136 after being installed without intervention by the patient or when the patient is not conscious, using the robotic arm 134. Thus, the workflow module may determine that the movement of the patient is not within expected parameters in block 808. For example, the workflow module can determine that the smart implant 136 restricts the ROM of the patient's knee to between 60° hyperextension and 120° flexion extension instead of an expected range of 30° and 165°. In this case, the workflow module may return to block 806 to again initiate the robotic telesurgery by inserting the smart implant 136 into another, more accurate position in the patient using the robotic arm 134.

At block 808, the workflow module can create a three-dimensional (3D) enveloped threshold in 3D space, which can then be used by the workflow module to continuously check/determine whether the patient is within the 3D enveloped threshold. This can be used to determine better and/or more accurate positioning of the smart implant relative to position of the patient. A surgeon, for example, would want to ensure that a patient's knee will pivot when the knee joint has been replaced with a smart implant. Therefore, the surgeon may desire to move the smart implant around and make sure it is in the right position while the surgeon is viewing the smart implant being moved into position. The 3D enveloped threshold can include the 3D object (e.g., the patient's knee, the smart implant, a combination of both, etc.). Using known information about how the 3D object is supposed to move, the surgeon can move the smart implant within the bounds of the 3D enveloped threshold to make sure that the patient's knee would have movement within that enveloped threshold. The workflow module can also analyze and compare 3D images of the surgical site against the envelope in 3D space to determine whether or not the tested movement is exceeding the 3D enveloped threshold.

Sometimes, the workflow module may determine that the movement of the smart implant 136 is within expected parameters. For example, the workflow module can determine that, based on sensor data received from the smart implant 136, the movement of the smart knee implant, by changing the position of the patient's leg, achieves the ROM of 30° to 165°, as expected. Thus, the workflow module may proceed to block 810 to verify that the sensed data is within expected parameters by comparing the received data from the smart implant 136 against the historic data from the remote database 128. In some implementations, block 810 can be performed as part of the determination in block 808.

Further, the workflow module may send a verification notification that the smart implant 136 is operating within expected parameters to the operation module 118, at block 812.

FIG. 9 is a flowchart of a process 900 for operating a control transfer module for the robot surgical system. It should also be noted that in some implementations, one or more blocks in the process 900 may occur in one or more different orders. For example, two blocks shown in succession in the process 900 may in fact be executed substantially concurrently or in the reverse order, depending upon the functionality involved. In addition, the blocks described herein can be understood as representing decisions made by a hardware structure, such as a state machine. The process 900 can be performed by the remote doctor module 102. One or more blocks in the process 900 can also be performed by one or more other computer systems, computing devices, services, cloud-based systems, and/or cloud-based services. For illustrative purposes, the process 900 is described from the perspective of a control transfer module, which can be a sub-module of the operation module 118.

At first, the control transfer module may receive a prompt from the operation module 118, at block 902. This prompt can indicate that the control transfer module may transfer control of the robotic telesurgery after the smart implant 136 has been inserted into the patient, from the surgeon at the remote doctor module 102 to a user device of staff in the OR (e.g., the OR module 104).

Further, the control transfer module may close the robotic telesurgery (e.g., implantation surgery) by instructing the OR module 104 to perform a post-operation procedure, at block 904. The control transfer module may direct the staff using the OR module 104 to complete the robotic telesurgery by closing the surgical site (e.g., stitching up the patient), ensuring that the patient has returned to normal state from anaesthetic, and checking whether the patient's vitals are normal. For example, the control transfer module can generate instructions that are presented at the OR module 104 directing the staff to close the smart knee implant surgical site and check vital parameters of Alex, such as, his heart-rate.

In block 906, the control transfer module may also determine if the smart implant 136 and its sensors 152A-N are transmitting data properly and operating as expected (e.g., according to predetermined parameters stored in one or more of the databases described herein). In some implementations, the control transfer module may determine that the smart implant 136 installed within the patient is not transmitting data properly according to desired conditions. For example, the control transfer module can determine that the smart knee implant is transmitting and indication that the ROM is 10° to 15°, which is not within the threshold range of 30° to 180° between flexion extension and hypertension, the force exerted by the smart knee implant can be detected as 50 lbs, and the detected temperature surrounding the smart implant can be 38 degrees Celsius, which is above a predetermined threshold temperature of 36.5 degrees Celsius. In this case, the control transfer module may return to block 904 and generate instructions to be presented at the OR module 104 that instructs the staff to perform one or more other post-operation procedures on the smart knee implant.

Sometimes, the control transfer module may determine that the smart implant 136 installed within the patient is transmitting data properly according to the expected parameters in block 906. In this case, the control transfer module may proceed to block 908 to verify the smart implant 136 calibration with the patient movement, sensed data from the sensors 152A-N of the smart implant 136, and historic data from the remote database 128. For example, the control transfer module can verify calibration that when Alex moves the left leg between the ROM of 30° to 50°, the smart knee implant has the ROM of 30° to 40°, which is less 10° less than the expected ROM of the smart knee implant with respect to the rest of Alex's left leg. Sometimes, the operation module 118 may provide correct values for the smart implant 136 and then retest the ROM of the smart implant 136. For example, the operation module 118 can provide the smart knee implant with the ROM of 30° to 50° between flexion extension and hyperextension with the force exerted by the smart knee implant as 120 lbs.

Moreover, the control transfer module may finish the implantation procedure by sending the verification of the smart implant 136 with the patient movement data, to the operation module 118, at block 910.

Figure 10:
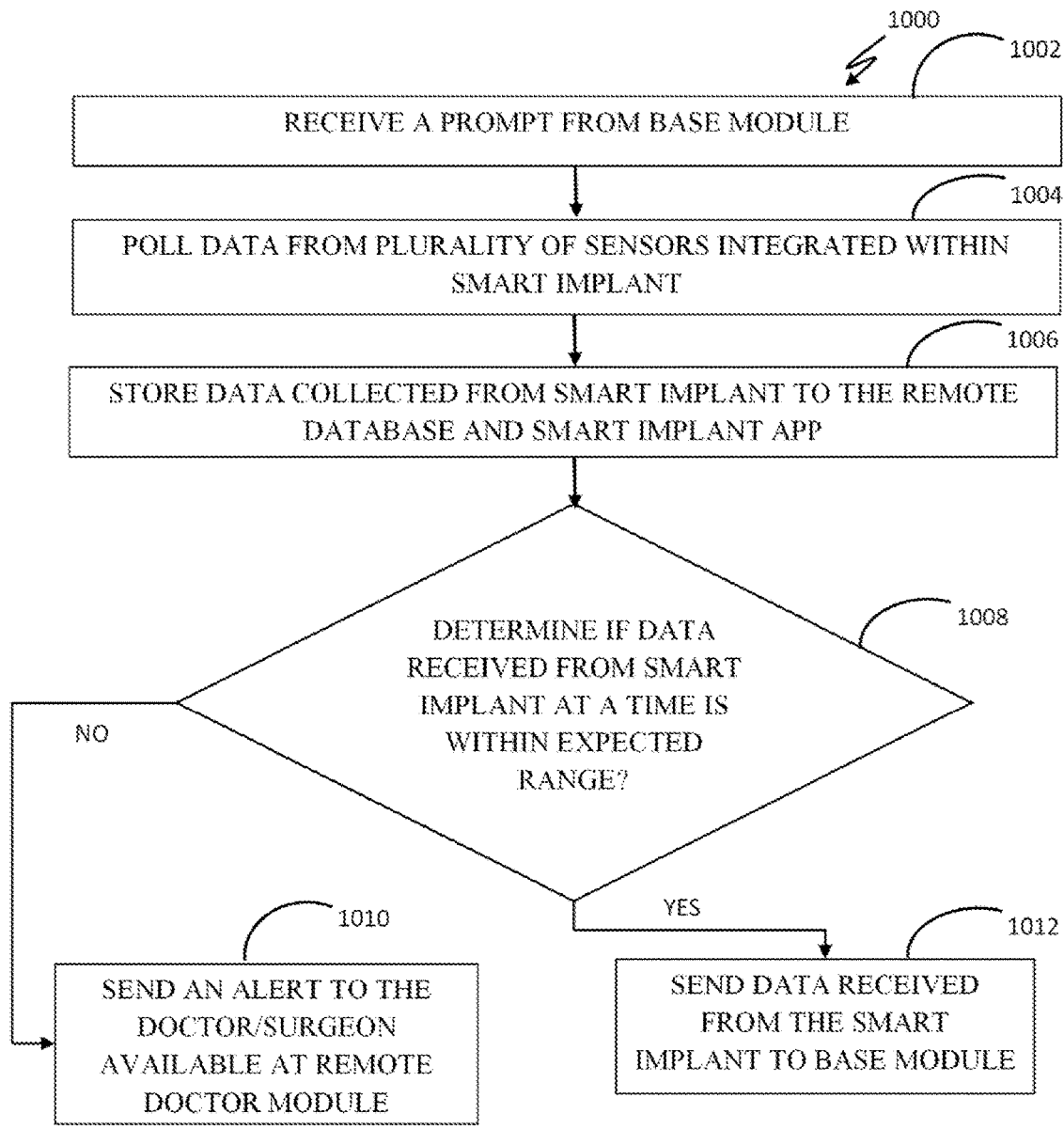
FIG. 10 is a flowchart of a process for operating a post-operative module for the robot surgical system.

FIG. 10 is a flowchart of a process 1000 for operating a post-operative module (e.g., the post-operative module 120) for the robot surgical system. It should also be noted that in some implementations, one or more blocks in the process 1000 may occur in one or more different orders. For example, two blocks shown in succession in the process 1000 may in fact be executed substantially concurrently in the reverse order, depending upon the functionality involved. In addition, the blocks described herein can be understood as representing decisions made by a hardware structure, such as a state machine. The process 1000 can be performed by the remote doctor module 102. One or more blocks in the process 1000 can also be performed by one or more other computer systems, computing devices, services, cloud-based systems, and/or cloud-based services. For illustrative purposes, the process 1000 is described from the perspective of the post-operative module 120.

At first, the post-operative module 120 may receive a prompt from the base module 114, at block 1002. The prompt can cause the post-operative module 120 to verify communication of the smart implant 136 with the smart implant application so that the doctor may review the robotic telesurgery remotely over the network(s) 106.

Further, the post-operative module 120 may poll data from the sensors 152A-N integrated within the smart implant 136, at block 1004. Sometimes, the sensors 152A-N may send the polled data directly from the smart implant 136 to the smart implant application. The sensors 152A-N, as described herein, may include, temperature sensors, ECG monitoring sensors, motion sensors, etc. For example, the post-operative module 120 can poll for data at a time interval of once every five minutes. The post-operative module 120 can poll for sensor data including average and maximum temperature and minimum and maximum ROM measurements during the time interval. The post-operative module 120 can also continuously poll for data and/or poll at one or more other predetermined periods of time.

The post-operative module 120 may store the data collected from the sensors 152A-N of the smart implant 136 to the remote database 128, at block 1006. The data can be stored in real-time. The data may also be stored in batch, for example, once all data is received after the time interval. In some implementations, the real-time transfer can refer to a near instantaneous transmission of data from the smart implant 136 directly to the remote database 128.

The post-operative module 120 may determine if the data received from the smart implant 136 is within expected ranges, at block 1008. Sometimes, the post-operative module 120 may determine that the data received from the smart implant 136 is not within expected ranges. For example, the post-operative module 120, at time 16:17:20 PM, can determine that the ROM of smart knee implant is 20° to 30°, which is not within a predetermined threshold range of 30° to 180° between flexion extension and hypertension, force exerted by the smart knee implant can be measured as 50 lbs, which is less than the threshold range of 100 lbs to 500 lbs, and a temperature sensor can detect a temperature of 38.4 degrees Celsius, which is more than the threshold temperature of 36.5 degrees Celsius. In this case, the post-operative module 120 may proceed to block 1010, to send an alert to the surgeon available at the remote doctor module 102. The notification can indicate what parameters are not within the expected ranges.

Sometimes, the post-operative module 120 may determine that the data received from the smart implant 136 at the particular time intervals are according to desired conditions in block 1008. For example, the post-operative module 120, at time of 16:17:20 PM, determines that the temperature sensor is detecting a temperature of 36.4 degrees Celsius, an ECG monitoring sensor detects bpm of 92, the smart knee implant is operating with the ROM of 30° to 150°, and the force exerted by the smart knee implant is 250 lbs. In this case, the post-operative module 120 may proceed to block 1012, to send the data received from the smart implant 136 to the base module 114.

Figure 11:
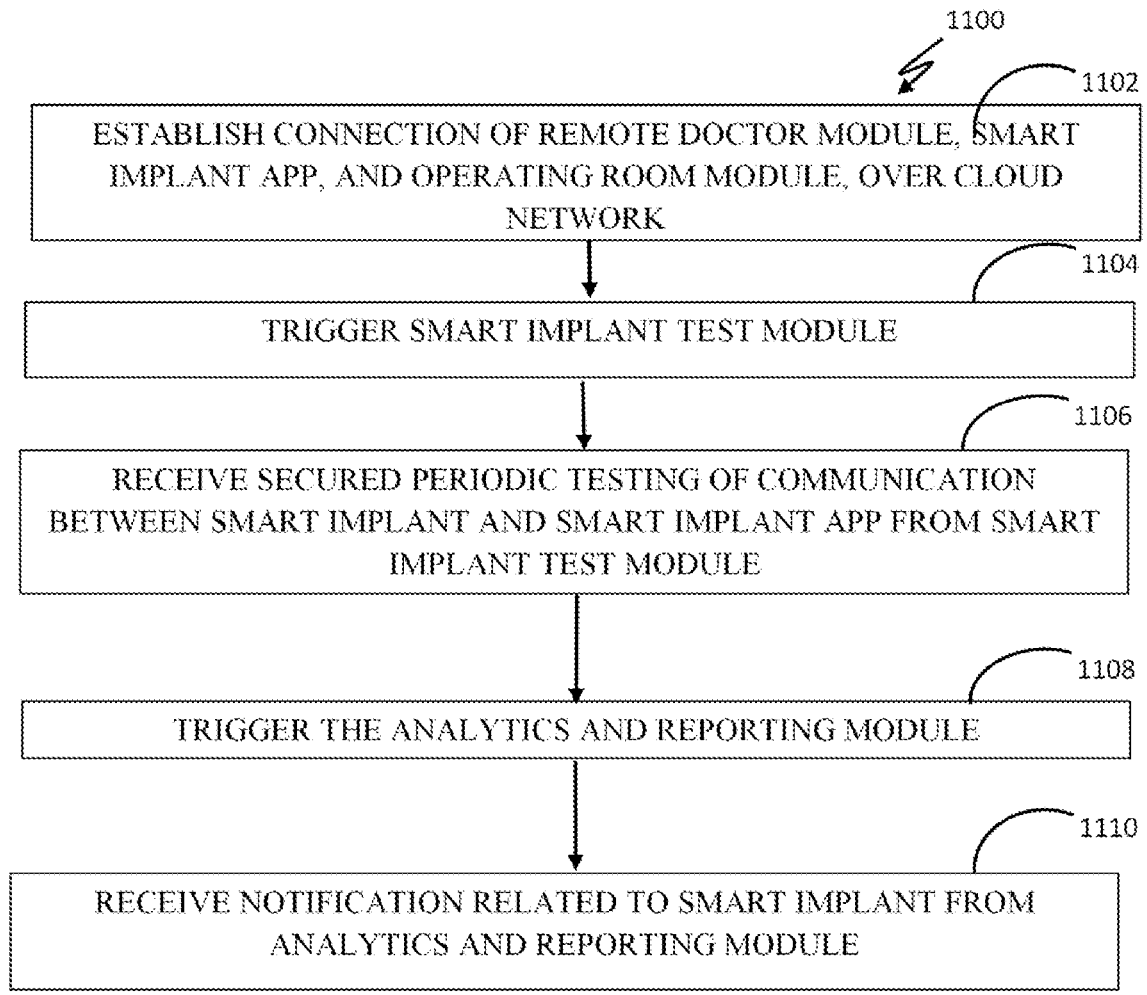
FIG. 11 is a flowchart of a process for operating a communication module of the robot surgical system.

FIG. 11 is a flowchart of a process 1100 for operating a communication module (e.g., the communication module 122) for the robot surgical system. The communication module 122 may perform operations related to facilitating communication between the OR module 104, the smart implant 136, the remote doctor module 102, and the user device 132, in parallel with the base module 114 (e.g., refer to FIG. 1B). Sometimes, the communication module 122 may employ one or more sub-modules to perform the operations of transmitting data and sending data in real-time, near real-time, or other time intervals. The sub-modules may include, but are not limited to, the smart implant test module 126, the analytics and reporting module 124, etc.

It should also be noted that in some implementations, one or more blocks in the process 1100 may occur in one or more different orders. For example, two blocks shown in succession in the process 1100 may in fact be executed substantially concurrently in the reverse order, depending upon the functionality involved. In addition, the blocks described herein can be understood as representing decisions made by a hardware structure, such as a state machine. The process 1100 can be performed by the remote doctor module 102. One or more blocks in the process 1100 can also be performed by one or more other computer systems, computing devices, services, cloud-based systems, and/or cloud-based services. For illustrative purposes, the process 1100 is described from the perspective of the communication module 122.

At first, the communication module 122 may establish a connection between the remote doctor module 102, the smart implant application running on the user device 132, and the OR module 104 over the network(s) 106, at block 1102. The established connection can enable sending and receiving of data between sensors 152A-N of the smart implant 136, such as a smart knee implant, the OR module 104, and the remote doctor module 102.

Further, the communication module 122 may trigger the smart implant test module 126, at block 1104. The operation of the smart implant test module 126 is described in conjunction with FIG. 12.

The communication module 122 may receive results of the secured periodic testing from the communication between the smart implant 136 and the smart implant application, at step 1106. For example, the communication module 122 can receive, from the smart implant test module 126, a notification that the smart implant application, at time 16:17:20 PM, received, a temperature value of 36.4 degrees Celsius, detected bpm of 92, and ROM of the smart knee implant being 30° to 155°.

Successively, the communication module 122 may trigger the analytics and reporting module 124, at block 1108. The operation of the analytics and reporting module 124 is described in conjunction with FIG. 13.

Figure 13:
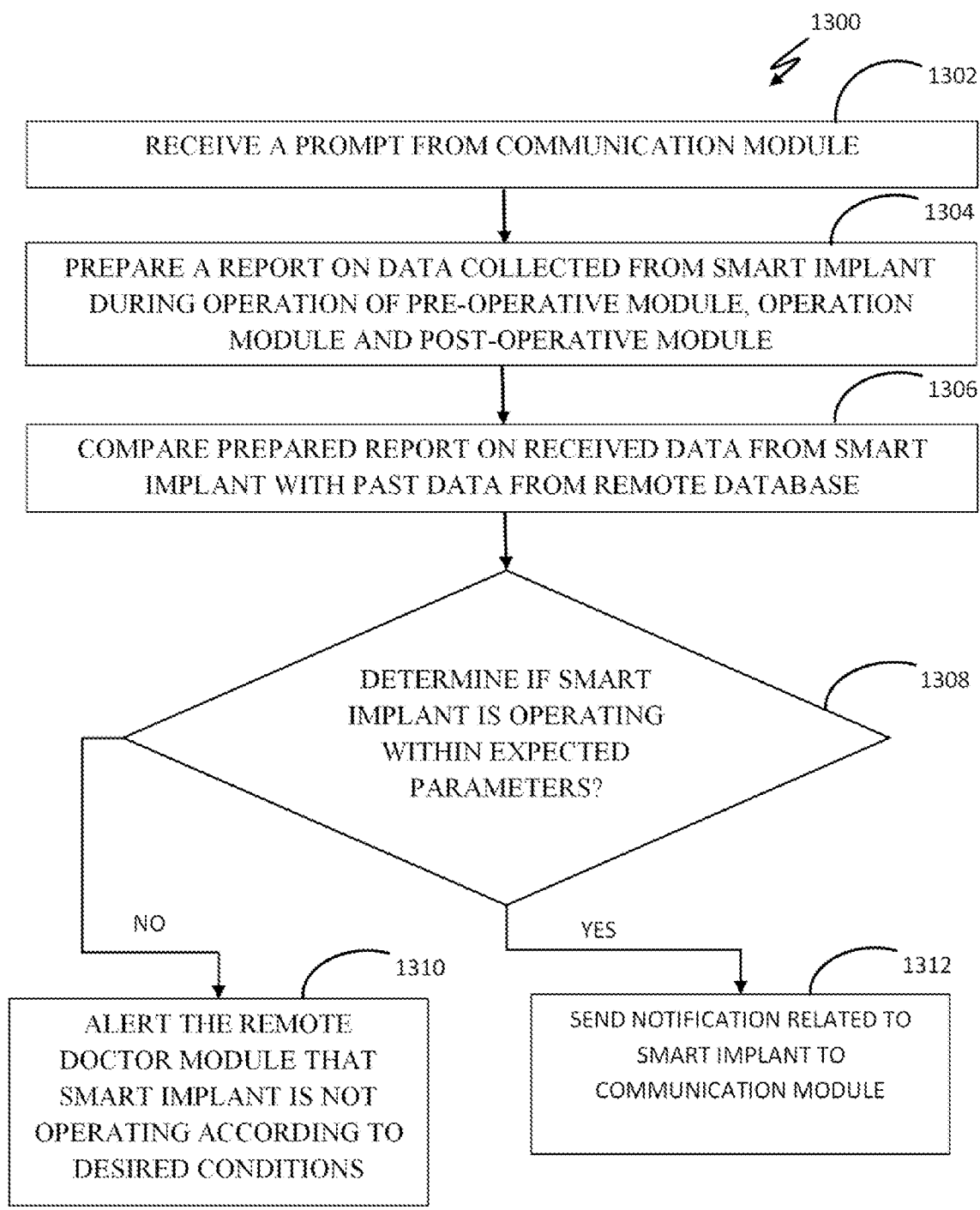
FIG. 13 is a flowchart of a process for operating an analytics and reporting module for the robot surgical system.

The communication module 122 may also receive a notification related to the smart implant 136 from the analytics and the reporting module 124, at block 1110, once the module 124 completes its analysis and reporting, as described in FIG. 13. For example, the communication module 122 can receive a notification of detected temperature surrounding the smart implant 136 that is within the expected temperature range. The communication module 122 can then transmit a notification to the user device 132 and/or the remote doctor module 102 indicating that the smart implant 136 is operating within the expected parameters.

Figure 12:
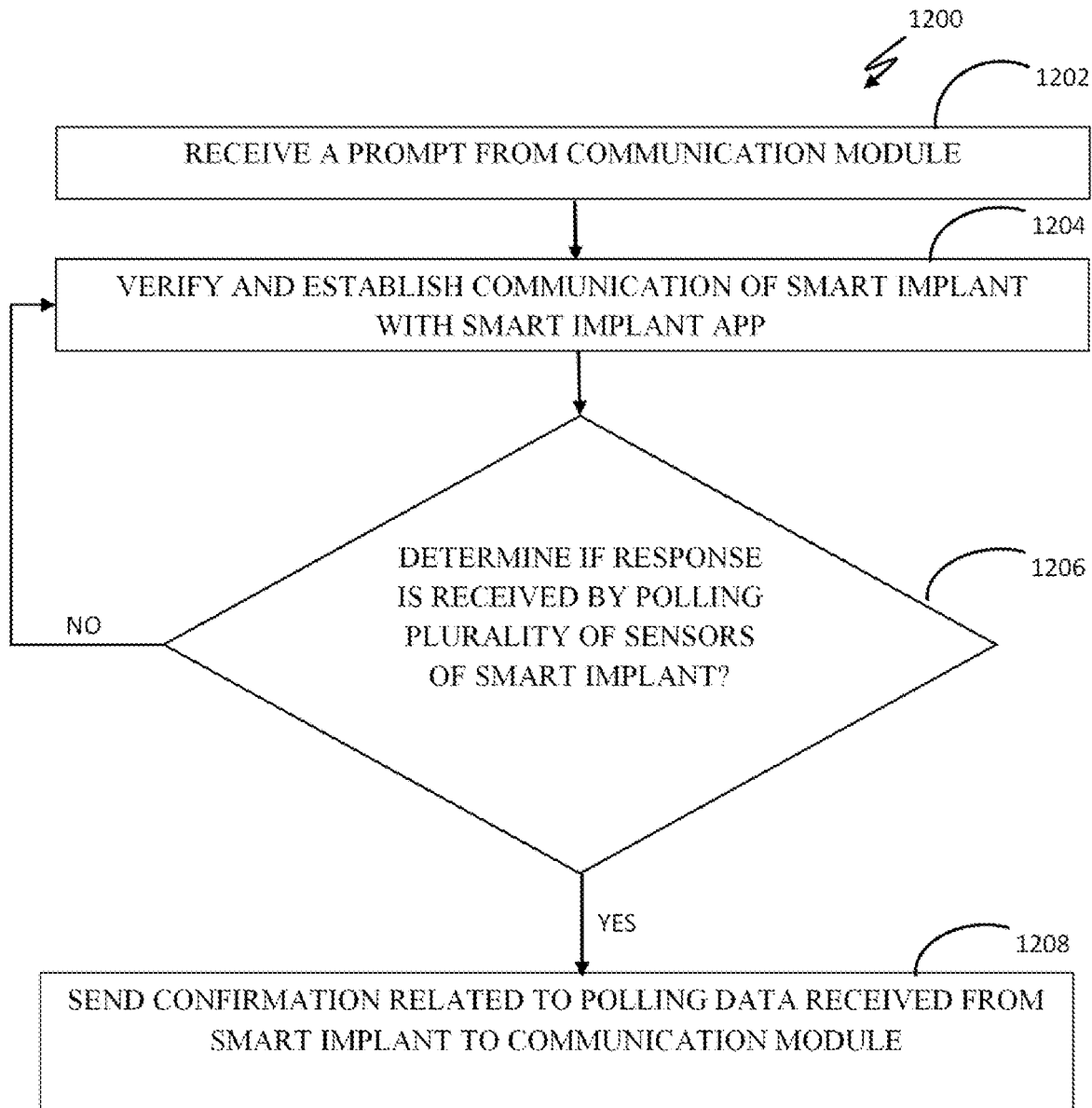
FIG. 12 is a flowchart of a process for operating a smart implant test module for the robot surgical system.

FIG. 12 is a flowchart of a process 1200 for operating a smart implant test module (e.g., the smart implant test module 126) for the robot surgical system It should also be noted that in some implementations, one or more blocks in the process 1200 may occur in one or more different orders. For example, two blocks shown in succession in the process 1200 may in fact be executed substantially concurrently in the reverse order, depending upon the functionality involved. In addition, the blocks described herein can be understood as representing decisions made by a hardware structure, such as a state machine. The process 1200 can be performed by the remote doctor module 102. One or more blocks in the process 1200 can also be performed by one or more other computer systems, computing devices, services, cloud-based systems, and/or cloud-based services. For illustrative purposes, the process 1200 is described from the perspective of the smart implant test module 126.

At first, the smart implant test module 126 may receive a prompt from the communication module 122, at block 1202 (e.g., refer to FIG. 11). The smart implant test module 126 may test an integrity of the communication between the remote doctor module 102 and the OR module 104 over the network(s) 106. The smart implant test module 126 may verify and establish communication between the sensors 152A-N integrated within the smart implant 136 and the smart implant application, at block 1204. The remote device may include, but is not limited to, a mobile device, a smartphone, a laptop, a tablet, etc. For example, the smart implant test module 126 can verify that the patient's cell phone is receiving data from the smart knee implant via the smart implant application in real-time, near real-time, or in one or more other predetermined time intervals.

The smart implant test module 126 may determine if a response is received over the smart implant application by polling the sensors 152A-N of the smart implant 136, at block 1206. The smart implant test module 126 may determine that the sensors 152A-N are transmitting data to the smart implant application. It can be noted that the smart implant test module 126 may poll the sensors 152A-N of the smart implant 136 and wait for a response over the smart implant application to verify the connection in block 1206.

Sometimes, the smart implant test module 126 may determine that the smart implant 136 is not transmitting data to the smart implant application and no response may be received from the smart implant 136 or the smart implant application. For example, at time 16:17:20 PM, the smart implant test module 126 may poll the temperature sensor within the smart knee implant 136 to determine temperature of the smart knee implant and the temperature sensor may not transmit the temperature reading to the smart implant application. In this case, the connection between sensors 152A-N of the smart implant 136 and the smart implant application may be lost. The smart implant test module 126 may return to block 1204 to again verify communication of the smart implant 136 with the smart implant application and re-establish communication of the sensors 152A-N and the smart implant application.

Sometimes, the smart implant test module 126 may determine that the smart implant 136 is transmitting data to the smart implant application and a response may be received. For example, the smart implant test module 126 can determine that the smart implant application, at time 16:17:20 PM, receives an indication from the temperature sensor of a temperature of 36.4 degrees Celsius, a bpm of 92 from the ECG monitoring sensor, and a ROM of the smart knee implant of 30° to 155°. Sometimes, the smart implant test module 126 may also repeat the polling of the sensors 152A-N of the smart implant 136. For example, at time 16:17:25 PM, the smart implant application can receive, from the temperature sensor, a temperature value of 36.2 degrees Celsius, a bpm of 90, and a ROM of the smart knee implant of 40° to 145°. The module 126 may also poll the sensors 152A-N for detected data at one or more predetermined time intervals.

The smart implant test module 126 may send a confirmation related to polling data received from the smart implant 136 to the communication module 122, at block 1208. For example, the smart implant test module 126 can send a confirmation that the sensors 152A-N of the smart implant 126 are transmitting sensed data to the smart implant application at one or more predetermined time intervals.

FIG. 13 is a flowchart of a process 1300 for operating an analytics and reporting module for the robot surgical system (e.g., the analytics and reporting module 124). It should also be noted that in some implementations, one or more blocks in the process 1300 may occur in one or more different orders. For example, two blocks shown in succession in the process 1300 may in fact be executed substantially concurrently in the reverse order, depending upon the functionality involved. In addition, the blocks described herein can be understood as representing decisions made by a hardware structure, such as a state machine. The process 1300 can be performed by the remote doctor module 102. One or more blocks in the process 1300 can also be performed by one or more other computer systems, computing devices, services, cloud-based systems, and/or cloud-based services. For illustrative purposes, the process 1300 is described from the perspective of the analytics and reporting module 124.

At first, the analytics and reporting module 124 may receive a prompt from the communication module 122, at block 1302 (e.g., refer to FIG. 11). The prompt can cause the analytics and reporting module 124 to collect data from the sensors 152A-N of the smart implant 136 and provide alerts when the smart implant 136 may be moved in a manner not expected or out of desired conditions/parameters during the robotic telesurgery and/or after the robotic telesurgery. For example, the analytics and reporting module 124 may collect data from the smart implant 136 and provide alerts post-operatively.

The analytics and reporting module 124 may prepare a report on the data collected from the sensors 152A-N of the smart implant 136 during the operation of pre-operative module 116, operation module 118, and/or post-operation module 120, at block 1304. As an illustrative example, the report can include an average force loading as well as a maximum force loading measured by the sensors 152A-N of the smart implant 136. The report may additionally include a maximum operating angle of the smart implant 136 and/or other metrics that can be measured by the sensors 152A-N and/or determined by the analytics and reporting module 124 based on the sensed data.

The analytics and reporting module 124 may compare a prepared report about the received data with historic data from the remote database 128, at block 1306. For example, the sensors 152A-N of the smart implant 136 can detect data indicating that the average operating temperature is 30.7 degrees Celsius with a maximum measurement of 38 degrees Celsius, while historic data can indicate that the maximum operating temperature for similar implants is 40 degrees Celsius with an average temperature of 31 degrees Celsius.

Based on this comparison in block 1306, the analytics and the reporting module 124 may determine if the smart implant 136 is operating within expected parameters, at block 1308. The analytics and the reporting module 124 may determine that the smart implant 136 is not operating within expected parameters. For example, the analytics and the reporting module 124 can determine that the smart implant 136 reports an average operating temperature of 32 degrees Celsius with a maximum measurement of 41 degrees Celsius, while the expected data (e.g., the historic data) indicates that a maximum operating temperature for smart knee implants is 40 degrees Celsius with an average temperature of 31 degrees Celsius. In this case, the analytics and the reporting module 124 may proceed to block 1310, and generate an alert to be received by the remote doctor module 102. The alert may be a notification indicating the operating parameters of the smart implant 136. In response to receiving the alert, the surgeon at the remote doctor module 102 may consult the patient and request that he/she goes to an emergency room of a nearby healthcare facility to seek immediate care.

Sometimes, the analytics and the reporting module 124 may determine that the smart implant 136 is operating within expected parameters in block 1308. For example, the analytics and the reporting module 124 can determine that the smart implant 136 reports an average operating temperature of 30 degrees Celsius with a maximum measurement of 37 degrees Celsius, while the expected data indicates that the maximum operating temperature for smart knee implants is 40 degrees Celsius with an average temperature of 31 degrees Celsius. In this case, the analytics and the reporting module 124 may proceed to block 1312, to send a notification related to the smart implant 136 to the communication module 122. The notification can indicate that the sensors 152A-N and/or the smart implant 136 are operating according to desired operating conditions.

Figure 14:
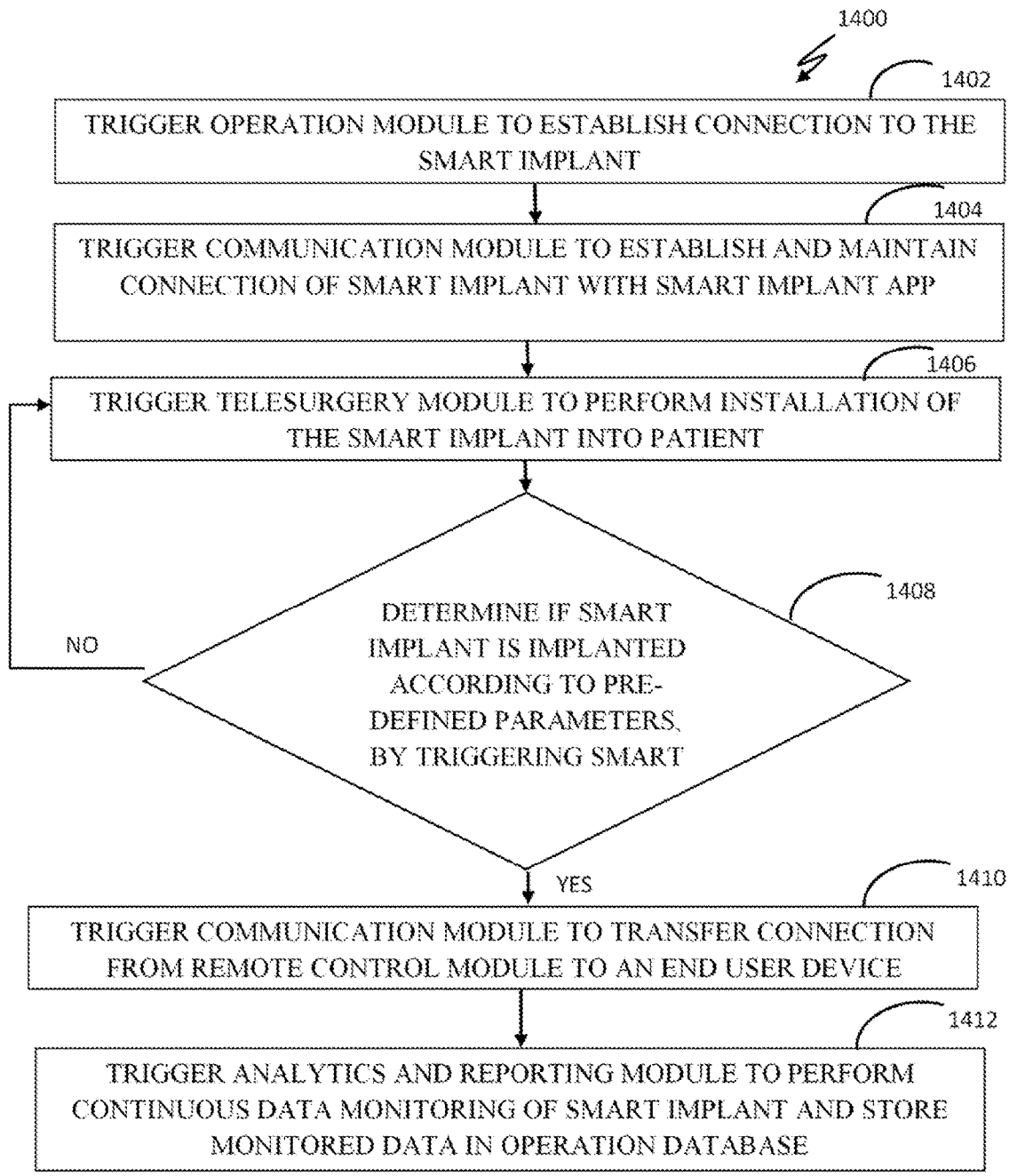
FIG. 14 is a flowchart of a process for operating a base module for the robot surgical system in an operating room.

FIG. 14 is a flowchart of a process 1400 for operating a base module (e.g., the base module 138) for the robot surgical system in an operating room. For example, the base module 138 of the OR module 104 may perform one or more operations in parallel with the base module 114 of the remote doctor module 102. For example, the base module 138 may collect data related to the smart implant 136 and the robotic telesurgery (e.g., the implantation procedure) during implanting. Further, the base module 138 of the OR module 104 may perform a handshake with the base module 114 of the remote doctor control 102.

It should also be noted that in some implementations, one or more blocks in the process 1400 may occur in one or more different orders. For example, two blocks shown in succession in the process 1400 may in fact be executed substantially concurrently in the reverse order, depending upon the functionality involved. In addition, the blocks described herein can be understood as representing decisions made by a hardware structure, such as a state machine. The process 1400 can be performed by the OR module 104. One or more blocks in the process 1400 can also be performed by one or more other computer systems, computing devices, services, cloud-based systems, and/or cloud-based services. For illustrative purposes, the process 1400 is described from the perspective of the base module 138.

At first, the base module 138 of the OR module 104 may trigger the operation module 118 to establish a connection with the smart implant 136, at block 1402. Further, the base module 138 may trigger the communication module 122 and the smart implant test module 126 to establish and maintain connection of the smart implant 136 with the smart implant application, at block 1404. For example, the base module 138 can establish connection of the smart knee implant over the smart implant application to transmit data related to the smart knee implant that by manipulating the orientation of the robotic arm 134 from 14 cm, 10 cm, 12 cm, to 13 cm, 12 cm, 11 cm, the ROM of the smart knee implant is 30° to 165° between flexion extension and hyperextension and the force exerted by the smart knee implant is 250 lbs, and the data transmission rate is 25 MBPS.

Further, the base module 138 may trigger the telesurgery module 140 to perform installation of the smart implant 136 into the patient, at block 1406. The base module 138 of the OR module 104 may receive instructions from the base module 114 of the remote doctor module 102 to proceed with the implantation surgery of the smart implant 136, by controlling orientation of the robotic arm 134, from the remote doctor module 102. For example, the base module 138 can generate instructions that adjust orientation of the robotic arm 134 from 14 cm, 10 cm, 12 cm to 13 cm, 12 cm, 12 cm, which adjusts orientation of the smart knee implant 136 to 12 cm, 12 cm, 11 cm.

Successively, the base module 138 may trigger the smart implant test module 126 to determine if the smart implant 136 is being implanted according to pre-defined parameters, at block 1408. The pre-defined parameters may be stored in the remote database 128 and may include, but are not limited to, orientation of the smart implant 136, speed of the smart implant 136, ROM of the smart implant 136, force exerted by the smart implant 136, orientation of the robotic arm 134, etc.

The base module 138 may determine that the smart implant 136 is not implanted according to pre-defined parameters. For example, the base module 138 can determine, based on data sensed by the sensors 152A-N of the smart implant 136, that the ROM of the smart knee implant is 20° to 25° between flexion extension and hyperextension, which is less than the threshold range of 30° to 180° for the smart knee implant and force exerted by the smart knee implant is 90 lbs, which is also less than the threshold range of 100 lbs to 500 lbs. In this case, the base module 138 may return to block 1406 to again trigger the telesurgery module 140 to perform installation of the smart implant 136 into the patient in such a way that ensures the smart implant 136 is implanted according to pre-defined parameters.

The base module 138 may determine that the smart implant 136 is implanted according to pre-defined parameters in block 1408. For example, the base module 138 can determine that the ROM of the smart knee implant is 40° to 115°, which is within the threshold range of 30° to 180° for the smart knee implant and the force exerted by the smart knee implant is 290 lbs, which is also within the threshold range of 100 lbs to 500 lbs. In this case, the base module 138 may proceed to block 1410 to trigger the communication module 122 to transfer a connection from the remote control module 102 to an end-user device. The end-user device may include a remote device for the patient with the smart implant application installed thereon to monitor operating conditions of the smart implant 136. It can be noted that the patient may have the end-user device such as, smartphone to continuously monitor the on-going conditions of the smart implant 136 once the robotic telesurgery is complete. The end-user device may be the user device 132, in some implementations.

As an illustrative example, the base module 138, after completing implanting, can transfer control to the patient's mobile phone so that the smart implant application at the mobile phone can present data that is detected by the sensors 152A-N of the smart implant 136 after the robotic telesurgery. Therefore, the patient can monitor parameters, such as temperature surrounding the smart implant 136, heartrate, ROM, force exerted, and other parameters described throughout this disclosure.

The base module 138 may also trigger the analytics and the reporting module 124 to perform continuous data monitoring of the smart implant 136 and store the monitored data in the operation database 142, at block 1412. Sometimes, the base module 138 may perform continuous monitoring of the smart implant 136 over the smart implant application and may store data monitored in real-time in the operation database 142. It can be noted that the base module 138 may transmit a notification/alert to the remote control module 102 when the smart implant 136 may not be operating according to the desired conditions, as described with regards to the communication module 122. The base module 138 may also perform a handshake with the base module 114 of the remote doctor module 102 to continuously update the operation database 142 and the remote database 128.

A number of vital signs monitoring devices are known that are capable of measuring multiple physiologic parameters of a patient wherein various sensor output signals are transmitted either wirelessly or by means of a wired connection to at least one remote site, such as a central monitoring station. A vital signs monitor can be integrated into the embodiments in a variety of manners.

Heart rate monitor refers to the sensor(s) and/or sensor system(s) that can be applied in the context of monitoring heart rates. Embodiments are intended to measure, directly or indirectly, any physiological condition from which any relevant aspect of heart rate can be gleaned. For example, some of the embodiments measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc. A heart rate monitor can be integrated into the embodiments in a variety of manners.

Pulse oximeter or SpO2 Monitor refers to a plethysmograph or any instrument that measures variations in the size of an organ or body part on the basis of the amount of blood passing through or present in the part. An oximeter is a type of plethysmograph that determines the oxygen saturation of the blood. One common type of oximeter is a pulse oximeter. A pulse oximeter is a medical device that indirectly measures the oxygen saturation of a patient's blood (as opposed to measuring oxygen saturation directly through a blood sample) and changes in blood volume in the skin. A pulse oximeter may include a light sensor that is placed at a site on a patient, usually a fingertip, toe, forehead, or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation. A pulse oximeter can be integrated into the embodiments in a variety of manners.

End Tidal CO2 monitor or capnography monitor refers to an instrument which is used for measurement of level of carbon dioxide (referred to as end tidal carbon dioxide, ETCO2) that is released at the end of an exhaled breath. End Tidal CO2 monitor or capnography monitor is widely used in anesthesia and intensive care. ETCO2 can be calculated by plotting expiratory CO2 with time. Further, ETCO2 monitor plays a very crucial role for the measurement of applications such as Cardiopulmonary Resuscitation (CPR), Airway assessment, Procedural sedation and analgesia, Pulmonary diseases such as obstructive pulmonary disease, pulmonary embolism, etc., heart failure, metabolic disorders, etc. The instrument can be configured as side stream (diverting) or mainstream (non-diverting). Diverting device transports, a portion of a patient's respired gases from the sampling site to the sensor while non-diverting device does not transport gas away. Also, measurement by the instrument is based on the absorption of infrared light by carbon dioxide; where exhaled gas passes through a sampling chamber containing an infrared light source and photodetector on both sides. Based on the amount of infrared light reaching the photodetector, the amount of carbon dioxide present in the gas can be calculated. An ETCO2 monitor or capnography monitor can be integrated into the embodiments in a variety of manners.

Blood pressure monitor refers to any instrument that measures blood pressure, particularly in arteries. Blood pressure monitors use a non-invasive technique (by external cuff application) or an invasive technique (by a cannula needle inserted in artery, used in operating theatre) for measurement, with non-invasive measurement being widely used. The non-invasive method (referred to as sphygmomanometer further) works by measurement of force exerted against arterial walls during ventricular systole (i.e., systolic blood pressure, occurs when heart beats and pushes blood through the arteries) and ventricular diastole (i.e., diastolic blood pressure, occurs when heart rests and is filling with blood) thereby measuring systole and diastole, respectively. It can be of three types automatic/digital, manual (aneroid-dial), and manual (mercury-column). The sphygmomanometer may include a bladder, a cuff, a pressure meter, a stethoscope, a valve, and a bulb. The cuff then inflates until it fits tightly around your arm, cutting off your blood flow, and then the valve opens to deflate it. It operates by inflating a cuff tightly around the arm, as the cuff reaches the systolic pressure, blood begins to flow around your artery, and creating a vibration which is detected by the meter, which records your systolic pressure. This systolic pressure is recorded. The techniques used for measurement may be: auscultatory or oscillometric. A blood pressure monitor can be integrated into the embodiments in a variety of manners.

Body temperature monitor refers to any instrument which is used for measurement of body temperature. The instrument can measure the temperature invasively or non-invasively by placement of sensor into organs such as bladder, rectum, esophagus, tympanum, esophagus, etc., and mouth, rectum, armpit, etc., respectively. The sensors are of two types: contact and non-contact. It can be measured in two forms: core temperature and peripheral temperature. Temperature measurement can be done by these sensing technologies: thermocouples, resistive temperature devices (RTDs, thermistors), infrared radiators, bimetallic devices, liquid expansion devices, molecular change-of-state, and silicon diodes. A thermometer which is a commonly used instrument for the measurement of temperature consists of a temperature sensing element (e.g., temperature sensor) and a means for converting to a numerical value. A blood temperature monitor can be integrated into the embodiments in a variety of manners.

Respiration rate or breathing rate is the rate at which breathing occurs and is measured by a number of breaths a person takes per minute. The rate is usually measured when a person is at rest and simply involves counting the number of breaths for one minute by counting how many times the chest rises. Normal respiration rates for an adult person at rest are in the range: 12 to 16 breaths per minute. A variation can be an indication of an abnormality/medical condition or a patient's demographic parameters. Hypoxia is a condition with low levels of oxygen in the cells and hypercapnia is a condition in which high levels of carbon dioxide in the bloodstream. Pulmonary disorders, asthma, anxiety, pneumonia, heart diseases, dehydration, drug overdose are some of the abnormal conditions which can bring a change to the respiration rate, thereby increasing or reducing the respiration rate from normal levels. Respiratory rate can be integrated into the embodiments in a variety of manners.

An electrocardiogram abbreviated as EKG or ECG refers to a representation of the electrical activity of the heart (graphical trace of voltage versus time) which is done by placement of electrodes on skin/body surface. The electrodes capture the electrical impulse which travels through the heart causing systole and diastole or the pumping of the heart. This impulse gives a lot of information related to the normal functioning of the heart and the production of impulses. A change may occur due to medical conditions such as arrhythmias (tachycardia where the heart rate becomes faster and bradycardia where the heart rate becomes slower), coronary heart disease, heart attacks, cardiomyopathy. The instrument used for the measurement of the electrocardiogram is called an electrocardiograph which measures the electrical impulses by the placement of electrodes on the surface of the body and represents the ECG by a PQRST waveform. PQRST wave is read as: P wave which represents the depolarization of the left and right atrium and corresponding to atrial contraction, QRS complex indicates ventricular depolarization and represents the electrical impulse as it spreads through the ventricles; T wave indicates ventricular repolarization and follows the QRS complex. An electrocardiogram can be integrated into the embodiments in a variety of manners.

Neuromonitoring also called Intraoperative neurophysiological monitoring (abbreviated as IONM) refers to an assessment of functions and changes in the brain, brainstem, spinal cord, cranial nerves, and peripheral nerves during a surgical procedure on these organs. It includes both continuous monitoring of neural tissue as well as the localization of vital neural structures. IONM measures changes in these organs which are indicative of irreversible damage, injuries in the organs, aiming at reducing the risk of neurological deficits after operations involving the nervous system. This has also been found to be effective in localization of anatomical structures, including peripheral nerves and sensorimotor cortex, which help in guiding the surgeon during dissection. Electrophysiological modalities which are employed in neuromonitoring are an extracellular single unit and local field recordings (LFP), Somatosensory Evoked Potential (SSEP), transcranial electrical motor evoked potentials (TCeMEP), Electromyography (EMG), electroencephalography (EEG), and auditory brainstem response (ABR). The use of neurophysiological monitoring during surgical procedures requires specific anesthesia techniques to avoid interference and signal alteration due to anesthesia. Neuromonitoring can be integrated into the embodiments in a variety of manners.

Motor Evoked Potential abbreviated as MEP refers to electrical signals which are recorded from descending motor pathways or muscles following stimulation of motor pathways within the brain. MEP may be calculated by measurement of the action potential which is elicited by non-invasive stimulation of the motor cortex through the scalp. MEP is a widely used technique for intraoperative monitoring and neurophysiological testing of the motor pathways specifically during spinal procedures. The technique of monitoring for measurement of MEP can be defined based on some of the parameters like a site of stimulation (motor cortex or spinal cord), method of stimulation (electrical potential or magnetic field), and site of recording (spinal cord or peripheral mixed nerve and muscle). The target site may be stimulated by the use of electrical or magnetic means. MEP can be integrated into the embodiments in a variety of manners.

Somatosensory evoked potential abbreviated as SSEP or SEP refers to the electrical signals which are elicited by the brain and the spinal cord in response to sensory stimulus or touch. SSEP is one of the most frequently used techniques for intraoperative neurophysiological monitoring in spinal surgeries. The method proves to be very reliable which allows for continuous monitoring during a surgical procedure. However, accuracy may be a concern at times in measurement. The sensor stimulus which is commonly given to the organs may be auditory, visual, or somatosensory SEPs and applied on the skin, peripheral nerves of the upper limb, lower limb, or scalp. The stimulation technique may be mechanical (widely used), or electrical (found to give larger and more robust responses), intraoperative spinal monitoring modality.

Somatosensory evoked potential can be integrated into the embodiments in a variety of manners.

Electromyography abbreviated as EMG refers to the evaluation and recording of electrical signals or electrical activity of the skeletal muscles. Electromyography instrument or Electromyograph or Electromyogram, the instrument for the measurement of the EMG activity works on a technique used for a recording of electrical activity produced by skeletal muscles and evaluation of the functional integrity of individual nerves. The nerves which are monitored by the EMG instrument may be intracranial, spinal, or peripheral nerves. The electrodes which may be used for the acquisition of signals may be invasive and non-invasive electrodes. The technique used for measurement may be spontaneous or triggered. Spontaneous EMG refers to the recording of myoelectric signals during surgical manipulation such as compression, stretching, or pulling of nerves produces; and does not perform external stimulation. Spontaneous EMG may be recorded by the insertion of a needle electrode. Triggered EMG refers to the recording of myoelectric signals during stimulation of target site such as pedicle screw with incremental current intensities. Electromyography can be integrated into the embodiments in a variety of manners.

Electroencephalography abbreviated as EEG refers to the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp where each pair of electrodes transmit a signal to one or more recording channels. It is one of the oldest and most commonly utilized modalities for intraoperative neurophysiological monitoring and assessing cortical perfusion and oxygenation during a variety of vascular, cardiac, and neurosurgical procedures. The waves produced by EEG are Alpha, Beta, Theta, and Delta. Electroencephalography can be integrated into the embodiments in a variety of manners.

Medical visualization systems refer to visualization systems that are used for visualization and analysis of objects (preferably three-dimensional (3D) objects). Medical visualization systems include the selection of points at surfaces, selection of a region of interest, selection of objects. Medical visualization systems may be used for applications diagnosis, treatment planning, intraoperative support, documentation, educational purpose. Medical visualization systems may consist of microscopes, endoscopes/arthroscopes/laparoscopes, fiber optics, surgical lights, high-definition monitors, operating room cameras, etc. 3D visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times. Medical visualization systems can be integrated into the embodiments in a variety of manners.

A microscope refers to an instrument that is used for viewing samples & objects that cannot be seen with an unaided eye. A microscope may have components eyepiece, objective lenses, adjustment knobs, stage, illuminator, condenser, diaphragm. A microscope works by manipulating how light enters the eye using a convex lens, where both sides of the lens are curved outwards. When light reflects off of an object being viewed under the microscope and passes through the lens, it bends towards the eye. This makes the object look bigger than it is. A microscope may be of types compound (light illuminated and the image seen with the microscope is two dimensional), dissection or stereoscope (light illuminated and image seen with the microscope is three dimensional), confocal (laser-illuminated and image seen with the microscope on a digital computer screen), Scanning Electron abbreviated as SEM (electron illuminated and image seen with the microscope in black and white), Transmission Electron Microscope abbreviated as TEM (electron illuminated and image seen with the microscope is the high magnification and high resolution). A microscope can be integrated into the embodiments in a variety of manners.

Endoscopes or arthroscopes or laparoscopes refer to minimally invasive surgical techniques where procedures are performed by performing minimal incision in the body. An Endoscope refers to an instrument to visualize, diagnose, and treat problems inside hollow organs where the instrument is inserted through natural body openings such as the mouth or anus. An endoscope may perform a procedure as follows: scope with a tiny camera attached to a long, thin tube is inserted. The doctor moves it through a body passageway or opening to see inside an organ. It can be used for diagnosis and surgery (such as for removing polyps from the colon). Arthroscope refers to an instrument to visualize, diagnose, and treat problems inside a joint by a TV camera inserted through small portals/incisions and perform procedures on cartilage, ligaments, tendons, etc. An endoscope may perform the procedure as follows: a surgeon makes a small incision in a patient's skin and inserts a pencil-sized instrument with a small lens and lighting system to magnify the target site (joint) and viewing of the interior of the joint by means of a miniature television camera and performing procedure. Endoscope refers to an instrument to visualize, diagnose, and treat problems inside soft organs like the abdomen and pelvis by a TV camera inserted through small portals/incisions and perform procedures. Endoscopes/arthroscopes/laparoscopes or minimally invasive surgery techniques can be integrated into the embodiments in a variety of manners.

Fiber optics refers to flexible, transparent fiber made by drawing glass (silica) or plastic to a diameter slightly thicker than that of a human hair. Fiber optics are arranged in bundles called optical cables and used to transmit light signals over long distances. Fiber optics are used most often as a means to transmit light between the two ends of the fiber and find wide usage in the medical field. Traditional surgery requires sizable and invasive incisions to expose internal organs and operate on affected areas and with fiber optics much smaller surgical incisions can be performed. Fiber optics contain components core, cladding, buffer coating. Fiber optics may be inserted in hypodermic needles and catheters, endoscope, operation theatres, ophthalmology, dentistry tools. Fiber optics sensors comprise a light source, optical fiber, external transducer, and photodetector. Fiberoptic sensors may be intrinsic or extrinsic. Fiber optics sensors may be categorized into four types physical, imaging, chemical, and biological. Fiber optics can be integrated into the embodiments in a variety of manners.

Surgical lights also referred to as operating light refers to an instrument that performs illumination of a local area or cavity of the patient. Surgical lights play an important role in illumination before, during, and after a medical procedure. Surgical lights may be categorized by lamp type as conventional (incandescent) and LED (light-emitting diode). Surgical lights may be categorized by mounting configuration as ceiling-mounted, wall-mounted, or floor stand. Surgical lights may be categorized by type as tungsten, quartz, and/or xenon halogens and light-emitting diodes (LEDs). Surgical lights include sterilizable handles which allow the surgeon to adjust light positions. Some important factors affecting surgical lights may be illumination, shadow management (cast shadows and contour shadows), the volume of light, heat management, fail-safe surgical lighting. Surgical lights can be integrated into the embodiments in a variety of manners.

High definition monitors refer to a display in which a clearer picture than possible with low-definition, low-resolution screens. High-definition monitors have a higher density of pixels per inch than past standard TV screens. Resolution for high definition monitors may be 1280×720 pixels or more. Full HD—1920×1080, Quad HD—2560×1440, 4K—3840×2160, 8K—7680×4320 pixels. High definition monitor may operate in progressive or interlaced scanning mode. High definition monitors used in medical applications may offer the following advantages improved visibility and allows for precise and safe surgery, rich color reproduction and provides suitable colors for each clinical discipline, better visibility, and operability with a large screen and electronic zoom, higher image quality in low light conditions, high contrast at high spatial frequencies, twice as sensitive as conventional sensors, easier determination of tissue boundaries (fat, nerves, vessels, etc.), better visualization of blood vessels and lesions. High definition monitors can be integrated into the embodiments in a variety of manners.

Operating room cameras refer to cameras that collect images from 360 degrees, and sensors that monitor both the operating room and people in it. Operating room cameras consist of cameras that are equipped in system and perform recording to give a bird's-eye view to the surgical team. Some cameras are on devices that surgeons insert through small incisions or orifices to see what they are doing during minimally invasive surgery. Operating room cameras may perform recording for this purpose: educational purposes: example—to broadcast a live feed of a surgical demonstration to a remote audience, to collect authentic footage for edited, instructional videos on a surgical technique or procedure; to facilitate video enhanced debriefing and coaching, or to formally assess surgical skills. Operating room cameras can be integrated into the embodiments in a variety of manners.

Surgical tower refers to an instrument used for performing minimally invasive surgery or surgery which is performed by creating small incisions in the body, therefore they are also referred to as minimally invasive devices or minimally invasive access devices. The procedure of performing minimally invasive surgery may be referred to as minimally invasive procedure or minimally invasive surgery, abbreviated as MIS. MIS is a safe, less invasive, and precise surgical procedure. Some of the advantages offered by surgical towers may be small incisions, less pain, low risk of infection, short hospital stays, quick recovery time, less scarring, and reduced blood loss. Some medical procedures where surgical towers are useful and are widely used may be lung procedures, gynecological, head and neck, heart, and urological conditions. MIS may be robotic or non-robotic/endoscopic. MIS may include the following: endoscopic, laparoscopic, arthroscopic, natural orifice intraluminal, and natural orifice transluminal procedures. A surgical tower access device may be designed as an outer sleeve and an inner sleeve that telescoping or slidably engages with one another. When a telescope is used to operate on the abdomen, the procedure is called laparoscopy. Surgical towers typically include access to a variety of surgical tools, such as, for example, electrocautery, radiofrequency, lasers, sensors, etc. A surgical tower can be integrated into the embodiments in a variety of manners.

Electrocautery refers to an instrument that is used for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision an electrocautery instrument may be used. For example: after removing part of the liver for removal of tumor etc., blood vessels in the liver must be sealed individually. An electrocautery instrument may be used for sealing living tissue such as arteries, veins, lymph nodes, nerves, fats, ligaments, and other soft tissue structures. It may be used in applications surgery, tumor removal, nasal treatment, wart removal. Electrocautery may operate in modes two monopolar or bipolar. The electrocautery instrument may consist of a generator, a handpiece, and one or more electrodes. Electrocautery can be integrated into the embodiments in a variety of manners.

Radiofrequency (RF) is used in association with minimally invasive surgery devices. The radiofrequency (RF) may be used for the treatment of skin by delivering it to the skin through a minimally invasive tool (fine needles) which does not require skin excision. The RF may be used for real-time tracking of minimally invasive surgery devices such as laparoscopic instruments. The RF may provide radiofrequency ablation to a patient suffering from atrial fibrillation through smaller incisions made between the ribs. The RF may be used to perform an endoscopic surgery on the body such as the spine by delivery of RF energy. Radiofrequency can be integrated into the embodiments in a variety of manners.

Laser is used in association with minimally invasive surgery devices. The laser may be used in minimally invasive surgeries with an endoscope. The laser is attached to the distal end of the endoscope and steers the laser at high speed by producing higher incision quality than existing surgical tools and minimizing damage to surrounding tissue. Laser may be used to perform minimally invasive surgeries using an endoscope, laparoscope in the lower and upper gastrointestinal tract, eye, nose, and throat. Lasers are used in minimally invasive surgery to ablate soft tissues, such as a herniated spinal disc bulge. Laser can be integrated into the embodiments in a variety of manners.

Sensors are used in association with minimally invasive surgery devices. The sensor may be used in minimally invasive surgeries for tactile sensing of tool—tissue interaction forces. During minimally invasive surgeries field of view and workspace of tools are compromised due to the indirect access to the anatomy and lack of surgeon's hand-eye coordination. The sensors provide a tactile sensation to the surgeon by providing information of shape, stiffness, and texture of organ or tissue (different characteristics) to surgeon's hands through a sense of touch. This detection of a tumor through palpation, which exhibit a 'tougher' feel than healthy soft tissue, pulse felt from blood vessels, and abnormal lesions. The sensors may provide in output shape, size, pressure, softness, composition, temperature, vibration, shear, and normal forces. Sensor may be electrical or optical, consisting of capacitive, inductive, piezoelectric, piezoresistive, magnetic, and auditory. The sensors may be used in robotic, laparoscopic, palpation, biopsy, heart ablation, and valvuloplasty. Sensors can be integrated into the embodiments in a variety of manners.

Imaging systems refer to techniques or instruments which are used for the creation of images and visualization of the interior of a human body for diagnostic and treatment purposes. Imaging systems play a crucial role in every medical setting and can help in the screening of health conditions, diagnosing causes of symptoms, monitor health conditions. Imaging systems may include various imaging techniques such as X-ray, Fluoroscopy, Magnetic resonance imaging (MRI), Ultrasound, Endoscopy, Elastography, Tactile imaging, Thermography, Medical photography, and Nuclear medicine e.g., Positron emission tomography (PET). Some factors which may drive the market are cost and clinical advantages of medical imaging modalities, a rising share of ageing populations, increasing prevalence of cardiovascular or lifestyle diseases, increasing demand from emerging economies. Some factors which may inhibit the market are saturation in many segments, high costs, lack of trained personnel. Imaging systems can be integrated into the embodiments in a variety of manners.

X-ray refers to a medical imaging instrument that uses X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of x-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type of tissue the X-rays pass through and their densities. Some of the applications where X-rays are used may be bone fractures, infections, calcification, tumors, arthritis, blood vessel blockages, digestive problems, heart problems. The X-ray instrument may consist of components such as an x-ray tube, operating console, collimator, grids, detector, radiographic film, etc. An X-ray can be integrated into the embodiments in a variety of manners.

Magnetic resonance imaging abbreviated as MRI refers to a medical imaging instrument that uses powerful magnets for the creation of images of the interior of the human body for diagnostic and treatment purposes. Some of the applications where MRI may be used may be brain/spinal cord anomalies, tumors in the body, breast cancer screening, joint injuries, uterine/pelvic pain detection, heart problems. For the creation of the image by an MM instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MM sensors. The time taken by the protons for realignment with the magnetic field, and energy release is dependent on environmental factors and the chemical nature of the molecules. MRI may more widely suit for imaging of non-bony parts or soft tissues of the body. MRI may be less harmful as it does not use damaging ionizing radiation as in the X-ray instrument. MM instrument may consist of magnets, gradients, radiofrequency system, computer control system. Some areas where imaging by MM should be prohibited may be people with implants. MM can be integrated into the embodiments in a variety of manners.

Computed tomography imaging abbreviated as CT refers to a medical imaging instrument that uses an X-ray radiation (i.e., X-ray range in the electromagnetic radiation spectrum) for the creation of cross-sectional images of the interior of the human body for diagnostic and treatment purposes. CT refers to a computerized x-ray imaging procedure in which a narrow beam of x-rays is aimed at a patient and quickly rotated around the body, producing signals that are processed by the machine's computer to generate cross-sectional images—or "slices"—of the body The CT instrument produces cross-sectional images of the body. Computed tomography instrument is different from an X-ray instrument as it creates 3-dimensional cross-sectional images of the body while X-ray creates 2-dimensional images of the body; the 3-dimensional cross-sectional images are created by taking images from different angles, which is done by taking a series of tomographic images from different angles. The different taken images are collected by a computer and digitally stacked to form a three-dimensional image of the patient. For creation of images by the CT instrument, a CT scanner uses a motorized x-ray source that rotates around the circular opening of a donut-shaped structure called a gantry while the x-ray tube rotates around the patient shooting narrow beams of x-rays through the body. Some of the applications where CT may be used may be blood clots, bone fractures, including subtle fractures not visible on X-ray, organ injuries. CT can be integrated into the embodiments in a variety of manners.

Stereotactic navigation systems refer to an instrument that uses patient imaging (e.g., CT, Mill) to guide surgeons in the placement of specialized surgical instruments and implants before and during a procedure. The patient images are taken to guide the physician before or during the medical procedure. The stereotactic navigation system includes a camera having infrared sensors to determine the location of the tip of the probe being used in the surgical procedure. This information is sent in real-time so that the surgeons have a clear image of the precise location of where they are working in the body. Stereotactic navigation systems may be framed (attachment of a frame to patient's head using screws or pins) or frameless (do not require the placement of a frame on the patient's anatomy). Stereotactic navigation systems may be used for diagnostic biopsies, tumor resection, bone preparation/implant placement, placement of electrodes, otolaryngologic, or neurosurgical procedures. Stereotactic navigation systems can be integrated into the embodiments in a variety of manners.

Ultrasound imaging also referred to as sonography or ultrasonography refers to a medical imaging instrument that uses ultrasound or sound waves (also referred to as acoustic waves) for the creation of cross-sectional images of the interior of the human body for diagnostic and treatment purposes. Ultrasound in the instrument may be produced by a piezoelectric transducer which produces sound waves and sends them into the body. The sound waves which are reflected are converted into electrical signals which are sent to an ultrasound scanner. Ultrasound instruments may be used for diagnostic and functional imaging. Ultrasound instruments may be used for therapeutic or interventional procedures. Some of the applications where ultrasound may be used are diagnosis/treatment/guidance during medical procedures e.g., biopsies, internal organs such as liver/kidneys/pancreas, fetal monitoring, etc., in soft tissues, muscles, blood vessels, tendons, joints. Ultrasound may be used for internal (transducer is placed in organs e.g., vagina) and external (transducer is placed on chest for heart monitoring or abdomen for the fetus). An ultrasound machine may consist of a monitor, keyboard, processor, data storage, probe, and transducer. Ultrasound can be integrated into the embodiments in a variety of manners.

Anesthesiology machine refers to a machine that is used to generate and mix medical gases like oxygen or air and anesthetic agents to induce and maintain anesthesia in patients. Anesthesiology machines deliver oxygen and anesthetic gas to the patient as well as filter out expiratory carbon dioxide. Anesthesia machine may perform following functions provides O2, accurately mix anesthetic gases and vapors, enable patient ventilation, and minimize anesthesia related risks to patients and staff. Anesthesia machine may consist of the following essential components a source of oxygen (O2), O2 flowmeter, vaporizer (anesthetics include isoflurane, halothane, enflurane, desflurane, sevoflurane, and methoxyflurane), patient breathing circuit (tubing, connectors, and valves), scavenging system (removes any excess anesthetics gases). Anesthesia machine may be divided into three parts the high pressure system, the intermediate pressure system, and the low-pressure system. The process of anesthesia starts with oxygen flow from pipeline or cylinder through the flowmeter, O2 flows through the vaporizer and picks up the anesthetic vapors, the O2-anesthetic mix then flows through the breathing circuit and into the patient's lungs, usually by spontaneous ventilation or normal respiration. The O2-anesthetic mix then flows through the breathing circuit and into the patient's lungs, usually by spontaneous ventilation or normal respiration. An anesthesiology machine can be integrated into the embodiments in a variety of manners.

Surgical bed is a bed equipped with mechanisms that can elevate or lower the entire bed platform, flex, or extend individual components of the platform, or raise or lower the head or the feet of the patient independently. Surgical bed may be an operation bed, cardiac bed, amputation Bed, fracture bed. Some essential components of a surgical bed may be bed sheet, woolen blanket, bath towel, bed block. Surgical beds can also be referred to as a postoperative bed, refers to a special type of bed made for the patient who is coming from the operation theatre or from another procedure that requires anesthesia. The surgical bed is designed in a manner that makes it easier to transfer an unconscious or weak patient from a stretcher/wheelchair to the bed. The surgical bed should protect bed linen from vomiting, bleeding, drainage, and discharges, provide warmth and comfort to the patient to prevent shock, provide necessary position, which is suitable for operation, protect patient from being chilled, prepared to meet any emergency. Surgical bed can be integrated into the embodiments in a variety of manners.

Disposable air warmer (also referred to as bair) refers to a convective temperature management system used in a hospital or surgery center to maintain a patient's core body temperature. The instrument consists of a reusable warming unit and a single-use disposable warming blankets for use during surgery and may also be used before and after surgery. The air warmer uses convective warming consisting of two components a warming unit and a disposable blanket. The air warmer filter air and then force warm air through disposable blankets which cover the patient. The blanket may be designed to use pressure points on the patient's body to prevent heat from reaching areas at risk for pressure sores or burns. The blanket may also include drain holes where fluid passes through the surface of the blanket to linen underneath which will reduce the risk of skin softening and reduce the risk of unintended cooling because of heat loss from evaporation. Disposable air warmer can be integrated into the embodiments in a variety of manners.

Sequential compression device abbreviated as SVD refers to an instrument that is used to help prevent blood clots in the deep veins of legs. The sequential compression device use cuffs around the legs that fill with air and squeeze your legs. This increases blood flow through the veins of your legs and helps prevent blood clots. A deep vein thrombosis (DVT) is a blood clot that forms in a vein deep inside the body. Some of the risks of using a DVT may be discomfort, warmth, or sweating beneath the cuff, skin breakdown, nerve damage, pressure injury. Sequential compression device can be integrated into the embodiments in a variety of manners.

Jackson frame refers to a frame or table which is designed for use in spine surgeries and may be used in a variety of spinal procedures in supine, prone, lateral positions in a safe manner. Two peculiar features of the Jackson table are no central table support and its ability to rotate the table through 180 degrees. The Jackson table is supported at both ends keeping the whole of the table free. This allows the visualization of trunk and major parts of extremities as well. The Jackson frame allows the patient to be slid from the cart onto the table in the supine position with appropriate padding placed. The patient is then strapped securely on the table. The Jackson frame can be integrated into the embodiments in a variety of manners.

Bed position controller refers to an instrument for controlling the position of the patient bed. Positioning a patient in bed is important for maintaining alignment and for preventing bed-sores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient may be in the following positions in a bed supine position, prone position, lateral position, sims position, fowler's position, semi-Fowler's position, orthopedic or tripod position, Trendelenburg position. Bed position controller can be integrated into the embodiments in a variety of manners.

Operating room environmental controls refers to control or maintenance of the environment in an operation theatre where procedures are performed to minimize the risk of airborne infection and provide a conducive environment for everyone in the operation theatre-surgeon, anesthesiologist, nurses & patient). Some factors which may contribute to poor quality in the environment of the operating room are temperature, ventilation, and humidity and they can lead to profound effects on the health of people in the operating room and work productivity. As an example: surgeons prefer a cool, dry climate since they work in bright, hot lights; anesthesia personnel prefer a warmer, less breezy climate; patient condition demands a relatively warm, humid, and quiet environment. Operating room environmental controls may control the environment by taking care of the following factors environmental humidity, infection, odor control. Humidity control may be done by controlling the temperature of anesthesia gases; Infection can be controlled by the use of filters to purify the air. Operating room environmental controls can be integrated into the embodiments in a variety of manners.

Heating, ventilation, and air conditioning (abbreviated as HVAC) refers to a system for regulating environment of indoor settings by moving air between indoor and outdoor areas, along with heating and cooling. HVAC may use a different combination of systems, machines, and technologies to improve comfort. HVAC may be necessary to maintain the environment of an operating room. HVAC for an operating room may be a traditional operating room (which may have a large diffuser array directly above the operating table) or a hybrid operating room (which may have monitors and imaging equipment that consume valuable ceiling space and complicate the design process). HVAC may consist of three main units heating unit (it may be a furnace or a boiler), a ventilation unit (it may be natural or forced), and an air conditioning unit (which may remove existing heat). HVAC may be made of components as air return, filter, exhaust outlets, ducts, electrical elements, outdoor unit, compressor, coils, and blower. The HVAC system may use central heating and AC systems that use a single blower to circulate air via internal ducts. Heating, ventilation, and air conditioning can be integrated into the embodiments in a variety of manners.

Air purification refers to a system for removing contaminants from the air in a room to improve indoor air quality. Air purification may be important in an operating room as surgical site infection may be a reason for high mortality and morbidity. The air purification system may deliver clean, filtered, contaminant-free air over the operating room table with diffuser, airflow, etc., to remove all infectious particles down and away from the patient. Air purification system may be air curtain, multi-diffuser array, or single large diffuser (based on laminar diffuser flow) or High-Efficiency Particulate Air filter. High-Efficiency Particulate Air filter referred to as HEPA filter protects from infection and contamination by a filter which is mounted at the terminal of the duct. HEPA filter may be mounted on the ceiling and deliver clean, filtered air in a flow to the room that provides a sweeping effect that pushes contaminants out via the return grilles that are usually mounted on the lower wall. Air purification can be integrated into the embodiments in a variety of manners.

Orthopedic tools also referred to as orthopedic instruments used for treatment and prevention of deformities and injuries of musculoskeletal system or skeleton, articulations, and locomotive system (i.e., set formed by skeleton, muscles attached to it and part of nervous system which controls the muscles). Major percentage of orthopedic tools are made of plastic. Orthopedic tools may be divided into the following specialties hand and wrist, foot and ankle, shoulder and elbow, arthroscopy, hip, and knee. Orthopedic tool may be fixation tools, relieving tools, corrective tools, compression-distraction tools. Fixation tool refers to a tool designed to restrict movements partially or completely in a joint, e.g., hinged splints (for preserving a certain range of movement in a joint), rigid splints. Relieving tool refers to a tool designed to relieve pressure on an ailing part by transferring support to healthy parts of an extremity, e.g., Thomas splint and the Voskoboinikova apparatus. Corrective tool refers to a tool designed to gradually correct a deformity, e.g., corsets, splints, orthopedic footwear, and insoles and other devices to correct abnormal positions of the foot. Compression-distraction tool refers to a tool designed to correct acquired or congenital deformities of the extremities, e.g., curvature, shortening, and pseudarthrosis such as Gudushauri. Fixation tools may be internal fixation tools (e.g., screws, plates) or external fixation tools (radius, tibia fracture fixation). Orthopedic tools may be bone-holding forceps, drill bits, nail pins, hammer staple, etc. Orthopedic tools can be integrated into the embodiments in a variety of manners.

Drill refers to a tool for making holes in bones for insertion of implants like nails, plates, screws, and wires. The drill tool functions by drilling cylindrical tunnels into bone. Drill may be used in orthopedics for performing medical procedures. Use of drill on bones may have some risks harm caused to bone, muscle, nerves, and venous tissues are wrapped by surrounding tissue, the drill does not stop immediately. Drills vary widely in speed, power, and size. Drill may be powered as electrical, pneumatic, or battery. Drills generally may work on speed below 1000 rpm in orthopedic. Temperature control of drill is an important aspect in the functioning of drill and is dependent on parameters rotation speed, torque, orthotropic site, sharpness of the cutting edges, irrigation, cooling systems. The drill may consist of components physical drill, cord power, electronically motorized bone drill, rotating bone shearing incision work unit. Drill can be integrated into the embodiments in a variety of manners.

Scalpel refers to a tool for slicing or cutting or osteotomy of bone during orthopedic procedure. The scalpel may be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate and performs cutting by an ultrasonically oscillating or forward/backward moving metal tip. Scalpel may prevent injuries caused by a drill in a spinal surgery such as complications such as nerve thermal injury, grasping soft tissue, tearing dura mater, and a mechanical injury may occur during drilling. Scalpel can be integrated into the embodiments in a variety of manners.

Stitches (also referred to as sutures) refers to a sterile, surgical thread used to repair cuts or lacerations and are used to close incisions or hold body tissues together after a surgery or an injury. Stitches may involve the use of a needle along with an attached thread. Stitches may be of type absorbable (the stitches automatically break down harmlessly in the body over time without intervention) and non-absorbable (the stitches do not automatically break down over time and must be manually removed if not left indefinitely). Stitches may be of type based on material monofilament, multifilament, and barb. Stitches may be classified based on size. Stitches may be of type based on material synthetic and natural. Stitches may be of type based on coating coated and un-coated. Stitches can be integrated into the embodiments in a variety of manners.

Stapler refers to a tool for fragment fixation when interfragmental screw fixation is not easy. When there is vast damage and bone is broken into fragments then staples can be used between these fragments for internal fixation and bone reconstruction. For example, they may be used around joints as in ankle and foot surgeries, in cases of soft tissue damage, to attach tendons or ligaments to the bone for reconstruction surgery. Stapler may be made of surgical grade stainless steel or titanium and they are thicker, stronger, and larger. The stapler can be integrated into the embodiments in a variety of manners.

Equipment refers to a set of articles, tools, or objects which help to implement or achieve an operation or activity. A medical equipment refers to an article, instrument, apparatus, or machine used for diagnosis, prevention, or treatment of a medical condition or disease or detection, measurement, restoration, correction, or modification of structure/function of the body for some health purpose. The medical equipment may perform functions invasively or non-invasively. The medical equipment may consist of components sensor/transducer, signal conditioner, display, data storage unit, etc. The medical equipment works by taking a signal from a measurand/patient, a transducer for converting one form of energy to electrical energy, signal conditioner such as an amplifier, filters, etc., to convert the output from the transducer into an electrical value, display to provide a visual representation of measured parameter or quantity, a storage system to store data which can be used for future reference. A medical equipment may perform any function of diagnosis or provide therapy, for example, the equipment delivers air/breaths into the lungs and moves it out of the lungs and out of lungs, to a patient who is physically unable to breathe, or breaths insufficiently. A medical equipment can be integrated into the embodiments in a variety of manners.

Ventilator (also referred to as a respirator) refers to an instrument that provides a patient with oxygen when they are unable to breathe on their own. The ventilator is required when a person is not able to breathe on their own. The ventilator may perform a function of pushing air into the lungs and allows it to come back out, gently like lungs when they are working. Ventilator functions by delivery of positive pressure to force air into your lungs, while usual breathing uses negative pressure by the opening of the mouth, and air flows in. The machine uses positive pressure to force air into your lungs. A ventilator may be required during surgery or after surgery. A ventilator may be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator may be used with a face mask (non-invasive ventilation, where the ventilation is required for a shorter duration of time) or with a breathing tube also referred to as an endotracheal tube (invasive ventilation, where the ventilation is required for a longer duration of time). A ventilator use may have some risks such as infections, fluid build-up, muscle weakness, lung damage, etc. A ventilator may be operated in modes ACV, SIMV, PCV, PSV, PCIRV, APRV, etc. A ventilator may have components gas delivery system, power source, control system, safety feature, gas filter, monitor. A ventilator can be integrated into the embodiments in a variety of manners.

Continuous positive airway pressure abbreviated as CPAP refers to an instrument which used for the treatment of sleep apnea disorder in a patient. Sleep apnea refers to a disorder in which breathing repeatedly stops and starts while a patient is sleeping, often because throat/airways briefly collapse or something temporarily blocks them and may lead to serious health problems, such as high blood pressure and heart trouble. Continuous positive airway pressure instrument helps the patient with sleep apnea to breathe more easily during sleep by sending a steady flow of oxygen into the nose and mouth during sleep, which keeps the airways open and helps to breathe normally. The CPAP machine may work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP may have a nasal pillow mask, nasal mask, or full mask. CPAP instrument may consist of components a motor, a cushioned mask, a tube that connects the motor to the mask, a headgear frame, adjustable straps. The essential components may be a motor, a cushioned mask, a tube that connects the motor to the mask. Continuous positive airway pressure instruments can be integrated into the embodiments in a variety of manners.

Consumables refer to necessary supplies for health systems to provide care within a hospital or surgical environment. Consumables may include gloves, gowns, masks, syringes, needles, sutures, staples, tubing, catheters, and adhesives for wound dressing, in addition to other tools needed by doctors and nurses to provide care. Depending on the device mechanical testing may be carried out in tensile, compression or flexure, in dynamic or fatigue, or impact or with the application of torsion. Consumables may be disposable (are time-saving, no risk of healthcare-associated infections, cost-efficient) or sterilizable (cross-contamination, risk of surgical site infections, sterilization). Consumables can be integrated into the embodiments in a variety of manners.

An Electronic Health Record (EHR) refers to a digital record of a patient's health information, which may be collected and stored systematically over time. It is an all-inclusive patient record and could include demographics, medical history, history of present illness (HPI), progress notes, problems, medications, vital signs, immunizations, laboratory data, and radiology reports. A computer software is used to capture, store, and share patient data in a structured way. The EHR may be created and managed by authorized providers and can make health information instantly accessible to authorized providers across practices and health organizations—such as laboratories, specialists, medical imaging facilities, pharmacies, emergency facilities, etc. The timely availability of EHR data can enable healthcare providers to make more accurate decisions and provide better care to the patients by effective diagnosis and reduced medical errors. Besides providing opportunities to enhance patient care, it may also be used to facilitate clinical research by combining all patients' demographics into a large pool. For example, the EHR data can support a wide range of epidemiological research on the natural history of disease, drug utilization, and safety, as well as health services research. The EHR can be integrated into the embodiments in a variety of manners.

Equipment tracking systems, such as RFID, refers to a system that tags an instrument with an electronic tag and tracks it using the tag. Typically, this could involve a centralized platform that provides details such as location, owner, contract, and maintenance history for all equipment in real-time. A variety of techniques can be used to track physical assets, including Radio-frequency Identification (RFID), Global Positioning System (GPS), Bluetooth Low Energy (BLE), barcodes, Near-Field Communication (NFC), Wi-Fi, etc. The equipment tracking system comprises the hardware components, such as RFID tags, GPS trackers, barcodes, and QR codes. The hardware component is placed on the asset, and it communicates with the software (directly or via a scanner), providing it with data about the asset's location and properties. An equipment tracking system uses electromagnetic fields to transmit data from an RFID tag to a reader. Reading of RFID tags may be done by portable or mounted RFID readers. RFID may be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by the use of barcode labels or using manual serial numbers and spreadsheets; however, these require manual labor. The RFID tag may be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own). Equipment tracking systems may offer advantages, no line of sight required, read Multiple RFID objects at once, scan at a distance, and flexibility. Equipment tracking systems, RFID can be integrated into the embodiments in a variety of manners.

Medical imaging systems typically use a wavelength of electromagnetic energy, or some other form of energy, such as ultrasound, magnetic resonance, etc., which when directed towards a subject, such as a bone tissue, soft tissues, or any object or any substance, etc., can image different types of tissues with varying depths of penetration. For instance, when visible light of a predefined wavelength is directed at a bone tissue, some part of incident light is absorbed by the bone tissue. As a result, the intensity of the reflected/refracted light is less than that of the incident light. The decrease in the intensity of the incident light may be measured and used to create an image. Today's medical science employs a variety of medical devices with such capabilities including, but not limited to, X-rays, magnetic resonance imaging (MM), ultrasound, angiography, computed tomography (CT), etc.

Figure 15:
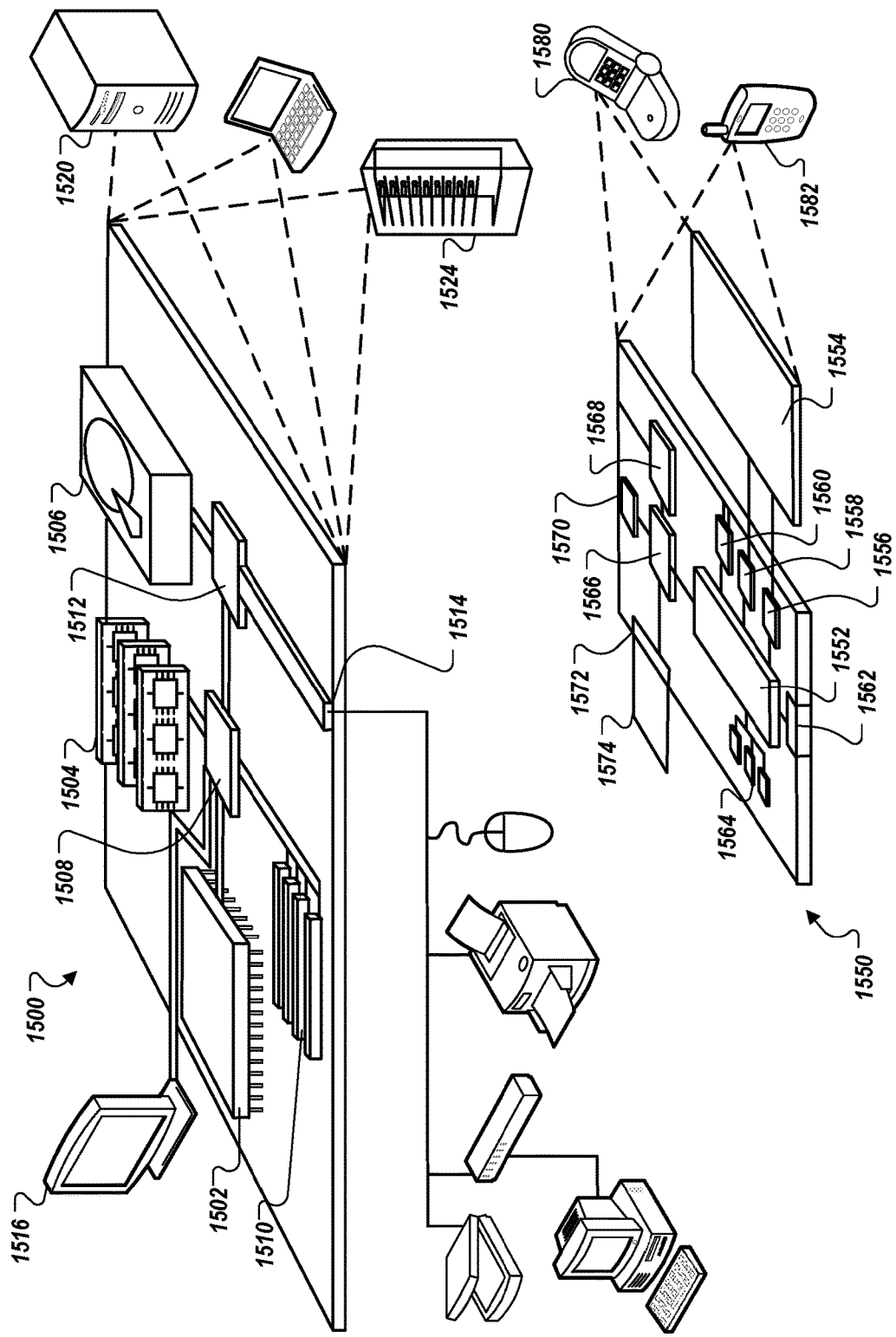
FIG. 15 is a schematic diagram that shows an example of a computing device and a mobile computing device.

FIG. 15 shows an example of a computing device 1500 and an example of a mobile computing device that can be used to implement the techniques described here. The computing device 1500 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and can be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1504 stores information within the computing device 1500. In some implementations, the memory 1504 is a volatile memory unit or units. In some implementations, the memory 1504 is a non-volatile memory unit or units. The memory 1504 can also be another form of computer-readable medium, such as a magnetic or optical disk.

The storage device 1506 is capable of providing mass storage for the computing device 1500. In some implementations, the storage device 1506 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1504, the storage device 1506, or memory on the processor 1502.

The high-speed interface 1508 manages bandwidth-intensive operations for the computing device 1500, while the low-speed interface 1512 manages lower bandwidth-intensive operations. Such allocation of functions is exemplary only. In some implementations, the high-speed interface 1508 is coupled to the memory 1504, the display 1516 (e.g., through a graphics processor or accelerator), and to the high-speed expansion ports 1510, which can accept various expansion cards (not shown). In the implementation, the low-speed interface 1512 is coupled to the storage device 1506 and the low-speed expansion port 1514. The low-speed expansion port 1514, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1500 can be implemented in a number of different forms, as shown in the figure. For example, it can be implemented as a standard server 1520, or multiple times in a group of such servers. In addition, it can be implemented in a personal computer such as a laptop computer 1522. It can also be implemented as part of a rack server system 1524. Alternatively, components from the computing device 1500 can be combined with other components in a mobile device (not shown), such as a mobile computing device 1550. Each of such devices can contain one or more of the computing device 1500 and the mobile computing device 1550, and an entire system can be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 can also be provided with a storage device, such as a micro-drive or other device, to provide additional storage. Each of the processor 1552, the memory 1564, the display 1554, the communication interface 1566, and the transceiver 1568, are interconnected using various buses, and several of the components can be mounted on a common motherboard or in other manners as appropriate.

The processor 1552 can execute instructions within the mobile computing device 1550, including instructions stored in the memory 1564. The processor 1552 can be implemented as a chipset of chips that include separate and multiple analog and digital processors. The processor 1552 can provide, for example, for coordination of the other components of the mobile computing device 1550, such as control of user interfaces, applications run by the mobile computing device 1550, and wireless communication by the mobile computing device 1550.

The processor 1552 can communicate with a user through a control interface 1558 and a display interface 1556 coupled to the display 1554. The display 1554 can be, for example, a TFT (Thin-Film-Transistor Liquid Crystal Display) display or an OLED (Organic Light Emitting Diode) display, or other appropriate display technology. The display interface 1556 can comprise appropriate circuitry for driving the display 1554 to present graphical and other information to a user. The control interface 1558 can receive commands from a user and convert them for submission to the processor 1552. In addition, an external interface 1562 can provide communication with the processor 1552, so as to enable near area communication of the mobile computing device 1550 with other devices. The external interface 1562 can provide, for example, for wired communication in some implementations, or for wireless communication in other implementations, and multiple interfaces can also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 can also be provided and connected to the mobile computing device 1550 through an expansion interface 1572, which can include, for example, a SIMM (Single In Line Memory Module) card interface. The expansion memory 1574 can provide extra storage space for the mobile computing device 1550, or can also store applications or other information for the mobile computing device 1550. Specifically, the expansion memory 1574 can include instructions to carry out or supplement the processes described above, and can include secure information also. Thus, for example, the expansion memory 1574 can be provide as a security module for the mobile computing device 1550, and can be programmed with instructions that permit secure use of the mobile computing device 1550. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1564, the expansion memory 1574, or memory on the processor 1552. In some implementations, the computer program product can be received in a propagated signal, for example, over the transceiver 1568 or the external interface 1562.

The mobile computing device 1550 can communicate wirelessly through the communication interface 1566, which can include digital signal processing circuitry where necessary. The communication interface 1566 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1568 using a radio-frequency. In addition, short-range communication can occur, such as using a Bluetooth, WiFi, or other such transceiver (not shown). In addition, a GPS (Global Positioning System) receiver module 1570 can provide additional navigation- and location-related wireless data to the mobile computing device 1550, which can be used as appropriate by applications running on the mobile computing device 1550.

The mobile computing device 1550 can also communicate audibly using an audio codec 1560, which can receive spoken information from a user and convert it to usable digital information. The audio codec 1560 can likewise generate audible sound for a user, such as through a speaker, e.g., in a handset of the mobile computing device 1550. Such sound can include sound from voice telephone calls, can include recorded sound (e.g., voice messages, music files, etc.) and can also include sound generated by applications operating on the mobile computing device 1550.

The mobile computing device 1550 can be implemented in a number of different forms, as shown in the figure. For example, it can be implemented as a cellular telephone 1580.

It can also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above.

What is claimed is:

1. A method of implanting a smart implant during a surgical procedure using a robotic surgical device, the method comprising:
    establishing, by a computing system, a connection between a smart implant and the computing system;
    before performing a surgical procedure that includes implanting the smart implant in a patient using a robotic surgical device, testing the smart implant using the robotic surgical device, wherein the testing comprises:
        transmitting, by the computing system, instructions to the robotic surgical device that cause the robotic surgical device to perform a smart implant action, wherein the smart implant action includes at least moving the smart implant through one or more physical movements identified by the instructions;
        receiving, by the computing system via the connection, smart implant action data from at least one sensor of the smart implant while the smart implant action is performed by the robotic surgical device; and
        validating, by the computing system, pre-surgical operation of the smart implant based, at least in part, on the smart implant action data;
    during the surgical procedure, validating intra-surgical operation of the smart implant as the smart implant is inserted into the patient by the robotic surgical device, wherein validating intra-surgical operation comprises:
        receiving, by the computing system, intra-surgical data sensed by the at least one sensor of the smart implant as the smart implant is inserted into the patient;
        comparing, by the computing system, the received intra-surgical data with target data for the surgical procedure; and
        validating, by the computing system, intra-surgical operation of the smart implant and correct placement of the smart implant within the patient based, at least in part, on the comparison of the intra-surgical data with the target data; and
    after the surgical procedure has been completed, validating post-surgical operation of the smart implant based, at least in part, on post-surgical data received from the smart implant.

2. The method of claim 1, wherein the surgical procedure comprises a robotic telesurgery procedure.

3. The method of claim 1, further comprising continuously verifying, by the computing system, the connection between the smart implant and the computing system before, during, and after the surgical procedure;
    wherein validating the pre-surgical operation of the smart implant is further based on the continuous verification of the connection before performing the surgical procedure;
    wherein validating the intra-surgical operation of the smart implant is further based on the continuous verification of the connection during the surgical procedure; and
    wherein validating the post-surgical operation of the smart implant is further based on the continuous verification of the connection after the surgical procedure.

4. The method of claim 1, wherein validating the pre-surgical operation of the smart implant comprises correlating detected movement of the smart implant based on the smart implant movement data with the instructions for moving the robotic surgical device.

5. The method of claim 1, wherein the robotic surgical device comprises a robotic arm that is controlled by the computing system.

6. The method of claim 1, wherein, during the pre-surgical testing and the intra-surgical operation validation, the computing system is remote from at least one of the patient, the smart implant, and the robotic surgical device during the testing.

7. The method of claim 1, wherein the robotic surgical device before the surgical procedure is the same robotic surgical device as during the surgical procedure.

8. The method of claim 1, wherein the testing of the smart implant occurs before the smart implant is inserted into the patient.

9. The method of claim 1, wherein the target data comprises one or more expected data values corresponding to one or more of the patient, the surgical robot, and the surgical procedure.

10. The method of claim 1, wherein the at least one sensor is at least one of a motion sensor, temperature sensor, and ECG monitoring sensor.

11. The method of claim 1, wherein validating the intra-surgical operation of the smart implant further comprises:
    receiving detected patient conditions during the surgical procedure from the at least one sensor of the smart implant;
    comparing the received patient conditions to expected patient conditions that are included in the target data; and
    determining, based on the comparison, whether the received patient conditions are within a threshold range of the expected patient conditions.

12. The method of claim 11, further comprising:
    in response to determining that the patient conditions are outside of the threshold range, generating, by the computing system, a notification indicating that the patient is trending outside of the threshold range and identifying corrective action to be taken.

13. The method of claim 12, wherein the corrective action includes removing the smart implant from the patient.

14. The method of claim 1, wherein after the surgical procedure, validating the post-surgical operation of the smart implant comprises:
- executing connection tests of the smart implant intermittently during one or more phases of closing the surgical procedure; and
- determining, at each phase of closing the surgical procedure, that the smart implant operates according to one or more expected threshold conditions based on the post-surgical data collected from the at least one sensor.

15. The method of claim 14, wherein the one or more phases of closing the surgical procedure comprise closing a surgical site of the patient, checking patient parameters, and waking up the patient from anesthesia.

16. The method of claim 14, further comprising generating, by the computing system, a notification that the smart implant does not operate according to the expected threshold conditions based on a determination that, at one of the phases, data collected from the at least one sensor is not received by the computing system, wherein the notification includes a corrective action.

17. The method of claim 16, wherein the corrective action includes stopping one or more remaining phases of closing the surgical procedure.

18. The method of claim 14, further comprising generating, by the computing system and based on the determination, a notification indicating that a next phase of closing the surgical procedure can be performed.

19. The method of claim 1, wherein after the surgical procedure, the smart implant is implanted inside the patient and is no longer retained by the robotic surgical device.

20. A system for implanting a smart implant during a surgical procedure using a robotic surgical device, the system comprising:
- a robotic surgical device configured to implant a smart implant into a patient during a surgical procedure; and
- a computer system in communication with the robotic surgical device and the smart implant, the computer system being configured to:
  - establish a connection between a smart implant and the computer system;
  - before performing a surgical procedure that includes implanting the smart implant in a patient using the robotic surgical device, test the smart implant using the robotic surgical device, wherein the testing comprises:
    - transmitting instructions to the robotic surgical device that cause the robotic surgical device to perform a smart implant action, wherein the smart implant action includes at least moving the smart implant through one or more physical movements identified by the instructions;
    - receiving, via the connection, smart implant action data from at least one sensor of the smart implant while the smart implant action is performed by the robotic surgical device; and
    - validating pre-surgical operation of the smart implant based, at least in part, on the smart implant action data;
  - during the surgical procedure, validate intra-surgical operation of the smart implant as the smart implant is inserted into the patient by the robotic surgical device, wherein validating intra-surgical operation comprises:
    - receiving intra-surgical data sensed by the at least one sensor of the smart implant as the smart implant is inserted into the patient;
    - comparing the received intra-surgical data with target data for the surgical procedure; and
    - validating intra-surgical operation of the smart implant and correct placement of the smart implant within the patient based, at least in part, on the comparison of the intra-surgical data with the target data; and
  - after the surgical procedure has been completed, validate post-surgical operation of the smart implant based, at least in part, on post-surgical data received from the smart implant.

* * * * *